(12) United States Patent
Wixey

(10) Patent No.: US 12,733,930 B2
(45) Date of Patent: Sep. 15, 2026

(54) SURGICAL STAPLING INSTRUMENT

(71) Applicant: INTUITIVE SURGICAL OPERATIONS, INC., Sunnyvale, CA (US)

(72) Inventor: Matthew Wixey, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/663,757

(22) Filed: May 14, 2024

(65) Prior Publication Data

US 2024/0293122 A1 Sep. 5, 2024

Related U.S. Application Data

(63) Continuation of application No. 17/602,272, filed as application No. PCT/US2020/025655 on Mar. 30, 2020, now Pat. No. 12,011,168.

(Continued)

(51) Int. Cl.
*A61B 17/072* (2006.01)
*A61B 34/30* (2016.01)
(Continued)

(52) U.S. Cl.
CPC ................... *A61B 17/07207* (2013.01); *A61B 2017/00477* (2013.01); *A61B 2017/0725* (2013.01);
(Continued)

(58) Field of Classification Search
CPC ............ A61B 17/072; A61B 17/07207; A61B 2017/0725; A61B 2017/07257;
(Continued)

(56) References Cited

U.S. PATENT DOCUMENTS 75,364 A 3/1868 Case
3,792,597 A 2/1974 Orain et al.
(Continued)

FOREIGN PATENT DOCUMENTS

AU 2014259544 A1 9/2015
CN 103889344 A 6/2014
(Continued)

OTHER PUBLICATIONS

International Search Report and Written Opinion for Application No. PCT/US2024/026826, mailed Jul. 26, 2024, 15 pages.

(Continued)

*Primary Examiner* — Linda J. Hodge
(74) *Attorney, Agent, or Firm* — Farber LLC

(57) ABSTRACT

A surgical instrument includes an elongate shaft and an end effector. The end effector includes a jaw, and a coupling member configured to receive a first and second reload and to removably couple the first and second reload to the end effector. The coupling member is configured to retain the first reload in a closed position relative to the jaw such that the jaw and the first reload have a tissue gap therebetween. The coupling member is configured to retain the second reload in a closed position relative to the jaw such that the jaw and the second reload have a tissue gap therebetween that is larger than the first tissue gap. The instrument is designed to accommodate reloads with different tissue gaps between the first jaw and the reload, thereby allowing an operator to treat tissue of varying sizes, shapes and thicknesses with the same surgical instrument.

9 Claims, 22 Drawing Sheets

Related U.S. Application Data

(60) Provisional application No. 62/835,086, filed on Apr. 17, 2019.

(51) Int. Cl.
*A61B 17/00* (2006.01)
*A61B 17/29* (2006.01)

(52) U.S. Cl.
CPC ............... *A61B 2017/07257* (2013.01); *A61B 2017/07271* (2013.01); *A61B 2017/2947* (2013.01); *A61B 34/30* (2016.02)

(58) Field of Classification Search
CPC ........... A61B 2017/07271; A61B 2017/07278; A61B 34/30; A61B 2017/07285; A61B 2017/00477; A61B 2017/2947
USPC ...................................................... 227/176.1
See application file for complete search history.

(56) References Cited

U.S. PATENT DOCUMENTS

| | | | |
|---|---|---|---|
| D231,902 | S | 6/1974 | Olson |
| D236,083 | S | 7/1975 | Robert |
| D236,427 | S | 8/1975 | Olson |
| 4,305,539 | A | 12/1981 | Korolkov et al. |
| 4,319,576 | A | 3/1982 | Rothfuss |
| 4,352,276 | A | 10/1982 | Smith |
| 4,403,892 | A | 9/1983 | Kane |
| 4,407,286 | A | 10/1983 | Noiles et al. |
| 4,429,695 | A | 2/1984 | Green |
| 4,509,518 | A | 4/1985 | McGarry et al. |
| 4,509,932 | A | 4/1985 | Weible |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,874 | A | 1/1987 | Chow et al. |
| 4,767,044 | A | 8/1988 | Green |
| 4,809,695 | A | 3/1989 | Gwathmey et al. |
| 4,848,637 | A | 7/1989 | Pruitt |
| 4,892,244 | A | 1/1990 | Fox et al. |
| 4,930,503 | A | 6/1990 | Pruitt |
| 4,978,049 | A | 12/1990 | Green |
| 5,007,300 | A | 4/1991 | Siva |
| 5,027,834 | A | 7/1991 | Pruitt |
| 5,040,715 | A | 8/1991 | Green et al. |
| 5,133,735 | A | 7/1992 | Slater et al. |
| 5,133,736 | A | 7/1992 | Bales, Jr. et al. |
| 5,142,931 | A | 9/1992 | Menahem |
| 5,147,357 | A | 9/1992 | Rose et al. |
| 5,180,092 | A | 1/1993 | Crainich |
| 5,242,457 | A | 9/1993 | Akopov et al. |
| 5,275,323 | A | 1/1994 | Schulze et al. |
| 5,307,976 | A | 5/1994 | Olson et al. |
| 5,312,023 | A | 5/1994 | Green et al. |
| 5,316,435 | A | 5/1994 | Mozingo |
| 5,334,183 | A | 8/1994 | Wuchinich |
| 5,342,395 | A | 8/1994 | Jarrett et al. |
| 5,342,396 | A | 8/1994 | Cook |
| 5,366,133 | A | 11/1994 | Geiste |
| 5,452,836 | A | 9/1995 | Huitema et al. |
| 5,452,837 | A | 9/1995 | Williamson, IV et al. |
| 5,465,895 | A | 11/1995 | Knodel et al. |
| 5,480,089 | A | 1/1996 | Blewett |
| 5,484,095 | A | 1/1996 | Green et al. |
| 5,484,451 | A | 1/1996 | Akopov et al. |
| 5,487,500 | A | 1/1996 | Knodel et al. |
| 5,497,931 | A | 3/1996 | Nakamura |
| 5,533,521 | A | 7/1996 | Granger |
| 5,540,375 | A | 7/1996 | Bolanos et al. |
| 5,554,164 | A | 9/1996 | Wilson et al. |
| 5,560,530 | A | 10/1996 | Bolanos et al. |
| 5,562,239 | A | 10/1996 | Boiarski et al. |
| 5,564,615 | A | 10/1996 | Bishop et al. |
| 5,571,116 | A | 11/1996 | Bolanos et al. |
| 5,571,285 | A | 11/1996 | Chow et al. |
| 5,573,534 | A | 11/1996 | Stone |
| 5,573,543 | A | 11/1996 | Akopov et al. |
| 5,607,449 | A | 3/1997 | Tontarra |
| 5,615,820 | A | 4/1997 | Viola |
| 5,624,452 | A | 4/1997 | Yates |
| 5,628,446 | A | 5/1997 | Geiste et al. |
| 5,632,432 | A | 5/1997 | Schulze et al. |
| 5,651,491 | A | 7/1997 | Heaton et al. |
| 5,652,849 | A | 7/1997 | Conway et al. |
| 5,667,626 | A | 9/1997 | Cayford et al. |
| 5,673,840 | A | 10/1997 | Schulze et al. |
| 5,673,842 | A | 10/1997 | Bittner et al. |
| 5,676,674 | A | 10/1997 | Bolanos et al. |
| 5,688,269 | A | 11/1997 | Newton et al. |
| 5,690,269 | A | 11/1997 | Bolanos et al. |
| 5,693,042 | A | 12/1997 | Boiarski et al. |
| 5,697,542 | A | 12/1997 | Knodel et al. |
| 5,700,270 | A | 12/1997 | Peyser et al. |
| 5,700,276 | A | 12/1997 | Benecke |
| 5,704,534 | A | 1/1998 | Huitema et al. |
| 5,709,680 | A | 1/1998 | Yates et al. |
| 5,738,474 | A | 4/1998 | Blewett |
| 5,752,644 | A | 5/1998 | Bolanos et al. |
| 5,752,973 | A | 5/1998 | Kieturakis et al. |
| 5,762,255 | A | 6/1998 | Chrisman et al. |
| 5,762,256 | A | 6/1998 | Mastri et al. |
| 5,779,130 | A | 7/1998 | Alesi et al. |
| 5,782,396 | A | 7/1998 | Mastri et al. |
| 5,792,135 | A | 8/1998 | Madhani et al. |
| 5,820,009 | A | 10/1998 | Melling et al. |
| 5,826,776 | A | 10/1998 | Schulze et al. |
| 5,833,695 | A | 11/1998 | Yoon |
| 5,865,361 | A | 2/1999 | Milliman et al. |
| 5,871,135 | A | 2/1999 | Williamson, IV et al. |
| 5,911,353 | A | 6/1999 | Bolanos et al. |
| 5,915,616 | A | 6/1999 | Viola et al. |
| 5,919,198 | A | 7/1999 | Graves, Jr. et al. |
| 5,941,442 | A | 8/1999 | Geiste et al. |
| 5,954,259 | A | 9/1999 | Viola et al. |
| 5,959,892 | A | 9/1999 | Lin et al. |
| 6,032,849 | A | 3/2000 | Mastri et al. |
| 6,050,996 | A | 4/2000 | Schmaltz et al. |
| 6,079,606 | A | 6/2000 | Milliman et al. |
| 6,113,598 | A | 9/2000 | Baker |
| 6,126,666 | A | 10/2000 | Trapp et al. |
| 6,174,309 | B1 | 1/2001 | Wrublewski et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,312,426 | B1 | 11/2001 | Goldberg et al. |
| 6,330,956 | B1 | 12/2001 | Willinger |
| 6,330,965 | B1 | 12/2001 | Milliman et al. |
| 6,443,973 | B1 | 9/2002 | Whitman |
| 6,488,196 | B1 | 12/2002 | Fenton, Jr. |
| 6,503,259 | B2 | 1/2003 | Huxel et al. |
| 6,582,451 | B1 | 6/2003 | Marucci et al. |
| 6,585,735 | B1 | 7/2003 | Frazier et al. |
| 6,644,532 | B2 | 11/2003 | Green et al. |
| 6,656,193 | B2 | 12/2003 | Grant et al. |
| 6,669,073 | B2 | 12/2003 | Milliman et al. |
| 6,692,363 | B1 | 2/2004 | Heutschi et al. |
| 6,770,072 | B1 | 8/2004 | Truckai et al. |
| 6,783,524 | B2 | 8/2004 | Anderson et al. |
| 6,786,382 | B1 | 9/2004 | Hoffman |
| 6,793,652 | B1 | 9/2004 | Whitman et al. |
| 6,817,974 | B2 | 11/2004 | Cooper et al. |
| 6,840,938 | B1 | 1/2005 | Morley et al. |
| 6,877,647 | B2 | 4/2005 | Green et al. |
| 6,905,057 | B2 | 6/2005 | Swayze et al. |
| 6,953,139 | B2 | 10/2005 | Milliman et al. |
| 6,955,608 | B1 | 10/2005 | Lutz |
| 6,959,852 | B2 | 11/2005 | Shelton, IV et al. |
| 6,964,363 | B2 | 11/2005 | Wales et al. |
| 6,978,921 | B2 | 12/2005 | Shelton, IV et al. |
| 6,978,922 | B2 | 12/2005 | Bilotti et al. |
| 6,981,941 | B2 | 1/2006 | Whitman et al. |
| 6,985,133 | B1 | 1/2006 | Rodomista et al. |

(56) References Cited

U.S. PATENT DOCUMENTS 6,986,451 B1 1/2006 Mastri et al.
6,988,649 B2 1/2006 Shelton, IV et al.
7,000,818 B2 2/2006 Shelton, IV et al.
7,000,819 B2 2/2006 Swayze et al.
7,044,352 B2 5/2006 Shelton, IV et al.
7,044,353 B2 5/2006 Mastri et al.
7,055,730 B2 6/2006 Ehrenfels et al.
7,055,731 B2 6/2006 Shelton, IV et al.
7,059,508 B2 6/2006 Shelton, IV et al.
7,070,083 B2 7/2006 Jankowski
7,114,642 B2 10/2006 Whitman
7,128,253 B2 10/2006 Mastri et al.
7,140,527 B2 11/2006 Ehrenfels et al.
7,140,528 B2 11/2006 Shelton, IV et al.
7,258,262 B2 8/2007 Mastri et al.
7,296,722 B2 11/2007 Ivanko
7,308,998 B2 12/2007 Mastri et al.
7,328,828 B2 2/2008 Ortiz et al.
7,380,695 B2 6/2008 Doll et al.
7,380,696 B2 6/2008 Shelton, IV et al.
7,398,908 B2 7/2008 Holsten et al.
7,401,721 B2 7/2008 Holsten et al.
7,407,075 B2 8/2008 Holsten et al.
7,455,676 B2 11/2008 Holsten et al.
7,472,814 B2 1/2009 Mastri et al.
7,481,349 B2 1/2009 Holsten et al.
7,491,202 B2 2/2009 Odom et al.
7,494,039 B2 2/2009 Racenet et al.
7,561,141 B2 7/2009 Shahoian et al.
7,565,993 B2 7/2009 Milliman et al.
7,588,174 B2 9/2009 Holsten et al.
7,654,431 B2 2/2010 Hueil et al.
7,658,312 B2 2/2010 Vidal et al.
7,673,783 B2 3/2010 Morgan et al.
7,699,835 B2 4/2010 Lee et al.
7,721,930 B2 5/2010 McKenna et al.
7,726,539 B2 6/2010 Holsten et al.
7,770,774 B2 8/2010 Mastri et al.
7,780,577 B2 8/2010 Arnold
7,794,475 B2 9/2010 Hess et al.
7,832,611 B2 11/2010 Boyden et al.
7,837,079 B2 11/2010 Holsten et al.
7,866,526 B2 1/2011 Green et al.
7,942,303 B2 5/2011 Shah et al.
7,950,561 B2 5/2011 Aranyi
8,070,035 B2 12/2011 Holsten et al.
8,083,118 B2 12/2011 Milliman et al.
8,127,975 B2 3/2012 Olson et al.
8,157,152 B2 4/2012 Holsten et al.
8,272,553 B2 9/2012 Mastri et al.
8,308,042 B2 11/2012 Aranyi
8,348,127 B2 1/2013 Marczyk
8,365,972 B2 2/2013 Aranyi et al.
8,371,492 B2 2/2013 Aranyi et al.
8,439,246 B1 5/2013 Knodel
8,490,851 B2 7/2013 Blier et al.
8,551,091 B2 10/2013 Couture et al.
8,573,465 B2 11/2013 Shelton, IV
8,579,178 B2 11/2013 Holsten et al.
8,608,047 B2 12/2013 Holsten et al.
8,672,206 B2 3/2014 Aranyi et al.
8,672,939 B2 3/2014 Garrison
8,685,016 B2 4/2014 Wham et al.
8,701,960 B1 4/2014 Manoux et al.
8,783,541 B2 7/2014 Shelton, IV et al.
8,800,841 B2 8/2014 Ellerhorst et al.
8,834,518 B2 9/2014 Faller et al.
8,851,355 B2 10/2014 Aranyi et al.
8,852,174 B2 10/2014 Burbank
8,858,547 B2 10/2014 Brogna
8,864,010 B2 10/2014 Williams
8,876,857 B2 11/2014 Burbank
8,905,287 B2 12/2014 Racenet et al.
8,925,785 B2 1/2015 Holsten et al.
9,010,606 B2 4/2015 Aranyi et al.
9,016,545 B2 4/2015 Aranyi et al.
9,055,961 B2 6/2015 Manzo et al.
9,161,807 B2 10/2015 Garrison
9,192,378 B2 11/2015 Aranyi et al.
9,192,379 B2 11/2015 Aranyi et al.
9,211,120 B2 12/2015 Scheib et al.
9,216,019 B2 12/2015 Schmid et al.
9,307,986 B2 4/2016 Hall et al.
9,316,267 B2 4/2016 Lenz et al.
9,345,479 B2 5/2016 Racenet et al.
9,498,215 B2 11/2016 Grant et al.
9,681,870 B2 6/2017 Baxter, III et al.
9,717,497 B2 8/2017 Zerkle et al.
9,717,498 B2 8/2017 Aranyi et al.
9,757,126 B2 9/2017 Cappola
9,777,459 B2 10/2017 Zuritis
9,808,246 B2 11/2017 Shelton, IV et al.
9,877,721 B2 1/2018 Schellin et al.
9,936,949 B2 4/2018 Measamer et al.
10,111,659 B2 10/2018 Racenet et al.
10,130,367 B2 11/2018 Cappola et al.
10,231,732 B1 3/2019 Racenet et al.
10,231,733 B2 3/2019 Ehrenfels et al.
10,285,693 B2 5/2019 Kimsey et al.
D850,617 S 6/2019 Shelton, IV et al.
10,335,147 B2 7/2019 Rector et al.
10,363,037 B2 7/2019 Aronhalt et al.
10,383,628 B2 8/2019 Kang et al.
10,646,219 B2 5/2020 Racenet et al.
10,722,233 B2 7/2020 Wellman
10,828,027 B2 11/2020 Racenet et al.
10,863,988 B2 12/2020 Patel et al.
10,912,556 B2 2/2021 Burbank
10,973,517 B2 4/2021 Wixey
11,014,224 B2 5/2021 Dey, IV et al.
11,020,138 B2 6/2021 Ragosta
11,166,773 B2 11/2021 Ragosta et al.
11,185,331 B2 11/2021 Adams et al.
11,191,542 B2 12/2021 Miller et al.
11,234,700 B2 2/2022 Ragosta et al.
11,266,409 B2 3/2022 Huitema et al.
11,291,445 B2 4/2022 Shelton, IV et al.
11,439,390 B2 9/2022 Patel et al.
D967,421 S 10/2022 Shelton, IV et al.
11,504,124 B2 11/2022 Patel et al.
11,517,312 B2 12/2022 Wixey
11,607,219 B2 3/2023 Shelton, IV et al.
11,642,129 B2 5/2023 Burbank
11,696,758 B2 7/2023 Murphy et al.
11,723,661 B2 8/2023 Wixey et al.
11,759,202 B2 9/2023 Morgan et al.
11,786,325 B2 10/2023 Mustufa et al.
11,806,015 B2 11/2023 Wixey et al.
11,857,188 B2 1/2024 Hites
11,864,762 B2 1/2024 Wixey
11,896,224 B2 2/2024 Wellman
11,903,583 B2 2/2024 Burbank et al.
11,944,301 B2 4/2024 Wixey et al.
11,944,302 B2 4/2024 Wixey et al.
11,986,184 B2 5/2024 Patel et al.
12,000,280 B2 6/2024 King
12,011,168 B2 6/2024 Wixey
D1,035,874 S 7/2024 Sun et al.
12,029,426 B2 7/2024 Millman et al.
12,029,473 B2 7/2024 Whitlock et al.
12,089,844 B2 9/2024 Patel et al.
12,137,903 B2 11/2024 Patel et al.
12,156,654 B2 12/2024 Wellman
D1,067,431 S 3/2025 Schings et al.
12,251,107 B2 3/2025 Wixey et al.
D1,070,086 S 4/2025 Yang et al.
12,262,891 B2 4/2025 Burbank
12,303,130 B2 5/2025 Wixey et al.
12,324,589 B2 6/2025 Kerver et al.
12,349,905 B2 7/2025 Wellman
12,359,696 B2 7/2025 Wixey
12,383,268 B2 8/2025 Wixey et al.
12,402,883 B2 9/2025 Yee et al.
D1,097,151 S 10/2025 Sun et al.

(56) References Cited

U.S. PATENT DOCUMENTS 12,508,024 B2 12/2025 Jasemian et al.
12,527,574 B2 1/2026 Hites
2002/0165562 A1 11/2002 Grant et al.
2002/0177843 A1 11/2002 Anderson et al.
2002/0188293 A1 12/2002 Manzo
2002/0188294 A1 12/2002 Couture et al.
2003/0078577 A1 4/2003 Truckai et al.
2003/0135204 A1 7/2003 Lee et al.
2003/0135205 A1 7/2003 Davenport et al.
2003/0144652 A1 7/2003 Baker et al.
2003/0171747 A1 9/2003 Kanehira et al.
2003/0181910 A1 9/2003 Dycus et al.
2004/0006340 A1 1/2004 Latterell et al.
2004/0049185 A1 3/2004 Latterell et al.
2004/0143263 A1 7/2004 Schechter et al.
2004/0232199 A1 11/2004 Shelton et al.
2004/0267310 A1 12/2004 Racenet et al.
2005/0006430 A1 1/2005 Wales
2005/0006434 A1 1/2005 Wales et al.
2005/0021027 A1 1/2005 Shields et al.
2005/0070925 A1 3/2005 Shelton, IV et al.
2005/0070958 A1 3/2005 Swayze et al.
2005/0101991 A1 5/2005 Ahlberg et al.
2005/0113826 A1 5/2005 Johnson et al.
2005/0171533 A1 8/2005 Latterell et al.
2005/0178813 A1 8/2005 Swayze et al.
2005/0187576 A1 8/2005 Whitman et al.
2005/0273084 A1 12/2005 Hinman et al.
2005/0273085 A1 12/2005 Hinman et al.
2006/0000868 A1 1/2006 Shelton, IV et al.
2006/0016853 A1 1/2006 Racenet
2006/0020287 A1 1/2006 Lee et al.
2006/0022014 A1 2/2006 Shelton, IV et al.
2006/0022015 A1 2/2006 Shelton, IV et al.
2006/0024817 A1 2/2006 Deguchi et al.
2006/0025809 A1 2/2006 Shelton, IV
2006/0025810 A1 2/2006 Shelton, IV
2006/0025811 A1 2/2006 Shelton, IV
2006/0025812 A1 2/2006 Shelton, IV
2006/0025813 A1 2/2006 Shelton et al.
2006/0025816 A1 2/2006 Shelton, IV
2006/0049230 A1 3/2006 Shelton, IV et al.
2006/0097026 A1 5/2006 Shelton, IV
2006/0111209 A1 5/2006 Hinman et al.
2006/0111210 A1 5/2006 Hinman
2006/0124689 A1 6/2006 Arad et al.
2006/0161190 A1 7/2006 Gadberry et al.
2006/0190031 A1 8/2006 Wales et al.
2006/0199999 A1 9/2006 Ikeda et al.
2006/0217706 A1 9/2006 Lau et al.
2006/0217709 A1 9/2006 Couture et al.
2006/0271042 A1 11/2006 Latterell et al.
2007/0010838 A1 1/2007 Shelton, IV et al.
2007/0045379 A1 3/2007 Shelton, IV
2007/0250113 A1 10/2007 Hegeman et al.
2007/0262116 A1 11/2007 Hueil et al.
2007/0270884 A1 11/2007 Smith et al.
2008/0023522 A1 1/2008 Olson et al.
2008/0029577 A1 2/2008 Shelton et al.
2008/0064572 A1 3/2008 Nardone
2008/0065100 A1 3/2008 Larkin
2008/0078804 A1 4/2008 Shelton et al.
2008/0086114 A1 4/2008 Schmitz et al.
2008/0093517 A1 4/2008 Chen
2008/0108446 A1 5/2008 Faude
2008/0161174 A1 7/2008 Lo
2008/0196533 A1 8/2008 Bergamasco et al.
2008/0210738 A1 9/2008 Shelton et al.
2008/0280736 A1 11/2008 D'Eredita
2008/0305934 A1 12/2008 Medina
2008/0308607 A1 12/2008 Timm et al.
2009/0090763 A1 4/2009 Zemlok et al.
2009/0181832 A1 7/2009 Bell
2009/0277947 A1 11/2009 Viola
2010/0006620 A1 1/2010 Sorrentino et al.
2010/0009818 A1 1/2010 Simonson et al.
2010/0057081 A1 3/2010 Hanna
2010/0057085 A1 3/2010 Holcomb et al.
2010/0076461 A1 3/2010 Viola et al.
2010/0076474 A1 3/2010 Yates et al.
2010/0096431 A1 4/2010 Smith et al.
2010/0108740 A1 5/2010 Pastorelli et al.
2010/0145334 A1 6/2010 Olson et al.
2010/0179545 A1 7/2010 Twomey et al.
2010/0198248 A1 8/2010 Vakharia
2010/0213240 A1 8/2010 Kostrzewski
2010/0331857 A1 12/2010 Doyle et al.
2011/0011915 A1 1/2011 Shelton, IV
2011/0017801 A1 1/2011 Zemlok et al.
2011/0022078 A1 1/2011 Hinman
2011/0036891 A1 2/2011 Zemlok et al.
2011/0042439 A1 2/2011 Johnson et al.
2011/0087238 A1 4/2011 Wang et al.
2011/0118707 A1 5/2011 Burbank
2011/0118778 A1 5/2011 Burbank
2011/0121049 A1 5/2011 Malinouskas et al.
2011/0121050 A1 5/2011 Nicholas et al.
2011/0139851 A1 6/2011 Mccuen
2011/0152879 A1 6/2011 Williams
2011/0174863 A1 7/2011 Shelton, IV et al.
2011/0186614 A1 8/2011 Kasvikis
2011/0204119 A1 8/2011 McCuen
2011/0251613 A1 10/2011 Guerra et al.
2011/0282339 A1 11/2011 Weizman et al.
2011/0288573 A1 11/2011 Yates et al.
2011/0290851 A1 12/2011 Shelton, IV
2011/0290853 A1 12/2011 Shelton, IV et al.
2011/0290854 A1 12/2011 Timm et al.
2011/0290855 A1 12/2011 Moore et al.
2011/0295269 A1 12/2011 Swensgard et al.
2011/0295270 A1 12/2011 Giordano et al.
2011/0301603 A1 12/2011 Kerr et al.
2011/0319886 A1 12/2011 Chojin et al.
2012/0000962 A1 1/2012 Racenet et al.
2012/0022584 A1 1/2012 Donnigan et al.
2012/0071891 A1 3/2012 Itkowitz et al.
2012/0205419 A1 8/2012 Weir et al.
2012/0209253 A1 8/2012 Donhowe
2012/0223121 A1 9/2012 Viola et al.
2012/0228358 A1 9/2012 Zemlok et al.
2012/0248167 A1 10/2012 Flanagan et al.
2012/0255986 A1 10/2012 Petty et al.
2012/0265241 A1 10/2012 Hart et al.
2012/0289999 A1 11/2012 Frank
2012/0298719 A1 11/2012 Shelton, IV et al.
2013/0015231 A1 1/2013 Kostrzewski
2013/0037597 A1 2/2013 Katre et al.
2013/0046303 A1 2/2013 Evans et al.
2013/0056521 A1 3/2013 Swensgard
2013/0068821 A1 3/2013 Huitema et al.
2013/0075448 A1 3/2013 Schmid et al.
2013/0087599 A1 4/2013 Krumanaker et al.
2013/0098965 A1 4/2013 Kostrzewski et al.
2013/0098966 A1* 4/2013 Kostrzewski .... A61B 17/07207 606/1
2013/0116668 A1 5/2013 Shelton, IV et al.
2013/0126586 A1 5/2013 Zhang et al.
2013/0148577 A1 6/2013 Terry et al.
2013/0240604 A1 9/2013 Knodel
2013/0248577 A1 9/2013 Leimbach et al.
2013/0256373 A1 10/2013 Schmid et al.
2013/0277410 A1 10/2013 Fernandez et al.
2013/0282052 A1* 10/2013 Aranyi ............ A61B 17/07207 606/208
2013/0296922 A1 11/2013 Allen, IV et al.
2013/0327808 A1 12/2013 Chen et al.
2013/0327809 A1 12/2013 Shelton, IV et al.
2014/0001236 A1 1/2014 Shelton, IV et al.
2014/0005653 A1 1/2014 Shelton, IV et al.
2014/0005654 A1 1/2014 Batross et al.
2014/0005662 A1 1/2014 Shelton, IV
2014/0005677 A1* 1/2014 Shelton, IV .......... B23K 26/38 219/121.72
2014/0021239 A1 1/2014 Kostrzewski

(56) References Cited

U.S. PATENT DOCUMENTS

2014/0025071 A1 1/2014 Sims et al.
2014/0027492 A1 1/2014 Williams
2014/0100569 A1 4/2014 Lawes et al.
2014/0100600 A1 4/2014 Kendrick
2014/0103093 A1 4/2014 Koch, Jr. et al.
2014/0110455 A1 4/2014 Ingmanson et al.
2014/0128867 A1 5/2014 Collings et al.
2014/0131418 A1 5/2014 Kostrzewski
2014/0175152 A1 6/2014 Hess et al.
2014/0180286 A1 6/2014 Marczyk et al.
2014/0183244 A1 7/2014 Duque et al.
2014/0200596 A1 7/2014 Weir et al.
2014/0200612 A1 7/2014 Weir et al.
2014/0200851 A1 7/2014 Weir et al.
2014/0214049 A1 7/2014 Jeong et al.
2014/0239036 A1 8/2014 Zerkle et al.
2014/0239044 A1 8/2014 Hoffman
2014/0239046 A1 8/2014 Milliman et al.
2014/0246477 A1 9/2014 Koch, Jr. et al.
2014/0249557 A1 9/2014 Koch, Jr. et al.
2014/0257331 A1 9/2014 Kim et al.
2014/0263546 A1 9/2014 Aranyi
2014/0263552 A1 9/2014 Hall et al.
2014/0263559 A1 9/2014 Williams et al.
2014/0263565 A1 9/2014 Lytle, IV et al.
2014/0263567 A1 9/2014 Williams et al.
2014/0263569 A1 9/2014 Williams et al.
2014/0276731 A1 9/2014 Voegele et al.
2014/0276776 A1 9/2014 Parihar et al.
2014/0284372 A1 9/2014 Kostrzewski
2014/0305989 A1 10/2014 Parihar et al.
2014/0309666 A1 10/2014 Shelton, IV et al.
2014/0343550 A1 11/2014 Faller et al.
2014/0343569 A1 11/2014 Turner
2014/0345971 A1 11/2014 Norris
2014/0364851 A1 12/2014 Batross et al.
2015/0018856 A1 1/2015 Poo et al.
2015/0073746 A1 3/2015 Gris et al.
2015/0088131 A1 3/2015 Weisshaupt et al.
2015/0141981 A1 5/2015 Price et al.
2015/0141993 A1 5/2015 Schechter et al.
2015/0173756 A1 6/2015 Baxter, III et al.
2015/0173789 A1 6/2015 Baxter, III et al.
2015/0209030 A1 7/2015 Kostrzewski et al.
2015/0209037 A1 7/2015 Kostrzewski et al.
2015/0250530 A1 9/2015 Manzo et al.
2015/0256609 A1 9/2015 Morton et al.
2015/0272575 A1 10/2015 Leimbach et al.
2015/0272576 A1 10/2015 Cappola
2015/0272583 A1 10/2015 Leimbach et al.
2015/0272606 A1 10/2015 Nobis
2015/0297227 A1 10/2015 Huitema et al.
2015/0297230 A1 10/2015 Schellin et al.
2015/0297235 A1 10/2015 Harris et al.
2015/0316431 A1 11/2015 Collins et al.
2015/0369277 A1 12/2015 Fevre et al.
2015/0374396 A1 12/2015 Strobl et al.
2016/0038227 A1 2/2016 Garrison
2016/0058441 A1 3/2016 Morgan et al.
2016/0058450 A1 3/2016 Shelton, IV et al.
2016/0066916 A1 3/2016 Overmyer et al.
2016/0089148 A1 3/2016 Harris et al.
2016/0120544 A1 5/2016 Shelton, IV et al.
2016/0157863 A1 6/2016 Williams et al.
2016/0157926 A1 6/2016 Boudreaux
2016/0166256 A1 6/2016 Baxter, III et al.
2016/0174973 A1 6/2016 Shelton, IV et al.
2016/0174977 A1 6/2016 Lytle, IV et al.
2016/0175033 A1 6/2016 Le
2016/0192999 A1 7/2016 Stulen et al.
2016/0199124 A1 7/2016 Thomas et al.
2016/0235473 A1 8/2016 Hagland
2016/0235489 A1 8/2016 Gombert et al.
2016/0242782 A1 8/2016 Shelton, IV et al.
2016/0249921 A1 9/2016 Cappola et al.
2016/0270780 A1 9/2016 Hall et al.
2016/0287251 A1 10/2016 Shelton, IV et al.
2016/0287316 A1 10/2016 Worrell et al.
2016/0296226 A1 10/2016 Kostrzewski
2016/0317216 A1 11/2016 Hermes et al.
2016/0338764 A1 11/2016 Krastins et al.
2016/0345971 A1* 12/2016 Bucciaglia ....... A61B 17/07207
2016/0374672 A1 12/2016 Bear et al.
2016/0374673 A1 12/2016 Stager et al.
2017/0010578 A1 1/2017 Miyakawa
2017/0042604 A1 2/2017 McFarland et al.
2017/0055981 A1 3/2017 Vendely et al.
2017/0056098 A1 3/2017 Crews et al.
2017/0065331 A1 3/2017 Mayer et al.
2017/0079710 A1 3/2017 Deville et al.
2017/0097035 A1 4/2017 Zimmerman et al.
2017/0105754 A1 4/2017 Boudreaux et al.
2017/0135746 A1 5/2017 Tetzlaff et al.
2017/0143335 A1 5/2017 Gupta et al.
2017/0156788 A1 6/2017 Johnson et al.
2017/0189028 A1 7/2017 Aranyi
2017/0202605 A1 7/2017 Shelton, IV et al.
2017/0231653 A1 8/2017 Kapadia
2017/0245857 A1 8/2017 Shelton, IV et al.
2017/0265865 A1 9/2017 Burbank
2017/0290584 A1 10/2017 Jasemian et al.
2017/0296172 A1 10/2017 Harris et al.
2017/0296173 A1 10/2017 Shelton, IV et al.
2017/0296183 A1 10/2017 Shelton, IV et al.
2018/0008265 A1 1/2018 Hatanaka et al.
2018/0021042 A1* 1/2018 Nicholas .......... A61B 17/07207
227/175.2
2018/0078268 A1 3/2018 Messerly et al.
2018/0125570 A1 5/2018 Rioux
2018/0161052 A1 6/2018 Weir et al.
2018/0168581 A1 6/2018 Hunter et al.
2018/0168585 A1 6/2018 Shelton, IV et al.
2018/0168607 A1 6/2018 Shelton, IV et al.
2018/0168620 A1 6/2018 Huang et al.
2018/0168622 A1 6/2018 Shelton, IV et al.
2018/0168628 A1 6/2018 Hunter et al.
2018/0168637 A1 6/2018 Harris et al.
2018/0168641 A1 6/2018 Harris et al.
2018/0168642 A1 6/2018 Shelton, IV et al.
2018/0168644 A1 6/2018 Shelton, IV et al.
2018/0168649 A1 6/2018 Shelton, IV et al.
2018/0168650 A1 6/2018 Shelton, IV et al.
2018/0206844 A1 7/2018 Harris et al.
2018/0214200 A1 8/2018 Nanditale et al.
2018/0232951 A1 8/2018 Alterovitz et al.
2018/0250085 A1 9/2018 Simi et al.
2018/0296213 A1 10/2018 Strobl
2018/0310948 A1 11/2018 Stamm et al.
2018/0317915 A1 11/2018 McDonald, II
2018/0353186 A1 12/2018 Mozdzierz et al.
2019/0000454 A1 1/2019 Swayze et al.
2019/0000525 A1 1/2019 Messerly et al.
2019/0015124 A1 1/2019 Williams et al.
2019/0029746 A1 1/2019 Dudhedia et al.
2019/0059894 A1 2/2019 Kumada et al.
2019/0076143 A1 3/2019 Smith
2019/0083086 A1 3/2019 Klaffenböck et al.
2019/0083819 A1 3/2019 Mitchell et al.
2019/0099181 A1* 4/2019 Shelton, IV ....... A61B 17/0682
2019/0125347 A1 5/2019 Stokes et al.
2019/0133571 A1 5/2019 Racenet et al.
2019/0142531 A1 5/2019 Wentworth et al.
2019/0150919 A1 5/2019 Williams et al.
2019/0192137 A1 6/2019 Shelton, IV et al.
2019/0201146 A1 7/2019 Shelton, IV et al.
2019/0231350 A1 8/2019 Scott et al.
2019/0239881 A1 8/2019 Laurent et al.
2019/0282233 A1 9/2019 Burbank et al.
2019/0290374 A1 9/2019 Ramadorai
2019/0298346 A1 10/2019 Shelton, IV et al.
2019/0298354 A1 10/2019 Shelton, IV et al.
2019/0298355 A1* 10/2019 Shelton, IV ..... A61B 17/07207
2019/0298356 A1 10/2019 Shelton, IV et al.
2019/0314107 A1 10/2019 Worrell et al.

(56) References Cited

U.S. PATENT DOCUMENTS

| | | | |
|---|---|---|---|
| 2019/0365458 | A1 | 12/2019 | Whitlock et al. |
| 2020/0054338 | A1 | 2/2020 | Shen |
| 2020/0205811 | A1 | 7/2020 | Posey et al. |
| 2020/0214706 | A1 | 7/2020 | Vendely et al. |
| 2020/0305872 | A1 | 10/2020 | Weidner et al. |
| 2021/0059670 | A1 | 3/2021 | Overmyer et al. |
| 2021/0153927 | A1 | 5/2021 | Ross et al. |
| 2021/0161529 | A1 | 6/2021 | Wixey |
| 2021/0177412 | A1 | 6/2021 | Wilson et al. |
| 2021/0177495 | A1 | 6/2021 | Ross et al. |
| 2021/0177500 | A1 | 6/2021 | Khalaji |
| 2021/0186494 | A1 | 6/2021 | Shelton, IV et al. |
| 2021/0196350 | A1 | 7/2021 | Fiebig et al. |
| 2021/0236119 | A1 | 8/2021 | Chavan et al. |
| 2021/0267596 | A1 | 9/2021 | Fanelli et al. |
| 2021/0290232 | A1 | 9/2021 | Harris et al. |
| 2021/0290233 | A1 | 9/2021 | Shelton, IV et al. |
| 2021/0386427 | A1 | 12/2021 | Millman et al. |
| 2022/0015823 | A1 | 1/2022 | Wilson et al. |
| 2022/0031346 | A1 | 2/2022 | Parks |
| 2022/0054130 | A1 | 2/2022 | Overmyer et al. |
| 2022/0061836 | A1 | 3/2022 | Parihar et al. |
| 2022/0071632 | A1 | 3/2022 | Patel et al. |
| 2022/0079585 | A1 | 3/2022 | Egan |
| 2022/0125428 | A1 | 4/2022 | Ragosta et al. |
| 2022/0142642 | A1 | 5/2022 | De Maillé et al. |
| 2022/0160358 | A1 | 5/2022 | Wixey |
| 2022/0167985 | A1 | 6/2022 | George et al. |
| 2022/0218344 | A1 | 7/2022 | Leimbach et al. |
| 2022/0296243 | A1 | 9/2022 | Nalagatla et al. |
| 2022/0304691 | A1 | 9/2022 | Fernandes et al. |
| 2022/0346790 | A1 | 11/2022 | Wellman |
| 2022/0378537 | A1 | 12/2022 | Hites et al. |
| 2022/0387027 | A1 | 12/2022 | Shelton, IV et al. |
| 2022/0395270 | A1 | 12/2022 | Patel et al. |
| 2023/0020577 | A1 | 1/2023 | Kerver et al. |
| 2023/0047784 | A1 | 2/2023 | Patel et al. |
| 2023/0099430 | A1 | 3/2023 | Schings et al. |
| 2023/0101993 | A1 | 3/2023 | Baril et al. |
| 2023/0120209 | A1 | 4/2023 | Parks et al. |
| 2023/0121658 | A1 | 4/2023 | Stokes et al. |
| 2023/0210527 | A1 | 7/2023 | Shelton, IV et al. |
| 2023/0225731 | A1 | 7/2023 | Burbank |
| 2023/0329711 | A1 | 10/2023 | Wixey et al. |
| 2024/0023961 | A1 | 1/2024 | Wixey et al. |
| 2024/0065690 | A1 | 2/2024 | Jasemian et al. |
| 2024/0081824 | A1 | 3/2024 | Hites |
| 2024/0108343 | A1 | 4/2024 | Wixey |
| 2024/0138834 | A1 | 5/2024 | Wellman |
| 2024/0188956 | A1 | 6/2024 | Swayze et al. |
| 2024/0252171 | A1 | 8/2024 | Wixey et al. |
| 2024/0260959 | A1 | 8/2024 | Wixey et al. |
| 2024/0315761 | A1 | 9/2024 | Whitlock et al. |
| 2024/0335194 | A1 | 10/2024 | Patel et al. |
| 2024/0341766 | A1 | 10/2024 | Millman et al. |
| 2024/0350143 | A1 | 10/2024 | Yee et al. |
| 2024/0407782 | A1 | 12/2024 | Patel et al. |
| 2025/0040930 | A1 | 2/2025 | Wellman |
| 2025/0261940 | A1 | 8/2025 | Wixey et al. |
| 2025/0295410 | A1 | 9/2025 | Wellman |
| 2025/0302472 | A1 | 10/2025 | Wixey et al. |
| 2025/0325275 | A1 | 10/2025 | Kerver et al. |
| 2025/0331857 | A1 | 10/2025 | Wixey et al. |
| 2025/0359870 | A1 | 11/2025 | Yee et al. |
| 2026/0020899 | A1 | 1/2026 | Khalaji |

FOREIGN PATENT DOCUMENTS

| | | | | |
|---|---|---|---|---|
| CN | 104042275 | A | 9/2014 | |
| CN | 105007836 | A | 10/2015 | |
| CN | 105769331 | A | 7/2016 | |
| CN | 106232026 | A | 12/2016 | |
| CN | 106491203 | A | 3/2017 | |
| CN | 107920819 | A | 4/2018 | |
| CN | 108024809 | A | 5/2018 | |
| CN | 112165909 | A | 1/2021 | |
| DE | 694747 | C | 8/1940 | |
| DE | 3724525 | C1 | 5/1988 | |
| DE | 102012103503 | A1 | 10/2013 | |
| EP | 0277532 | B1 | 8/1990 | |
| EP | 0469396 | A1 | 2/1992 | |
| EP | 0277529 | B1 | 4/1993 | |
| EP | 0641546 | A1 | 3/1995 | |
| EP | 0986336 | A1 | 3/2000 | |
| EP | 1090592 | A1 | 4/2001 | |
| EP | 1479348 | A1 | 11/2004 | |
| EP | 1728473 | A1 | 12/2006 | |
| EP | 1479346 | B1 | 1/2007 | |
| EP | 1621141 | B1 | 7/2007 | |
| EP | 2374419 | A2 | 10/2011 | |
| EP | 1316290 | B1 | 2/2012 | |
| EP | 2517639 | A1 | 10/2012 | |
| EP | 2540231 | A2 | 1/2013 | |
| EP | 1754445 | B1 | 10/2013 | |
| EP | 2774548 | A2 | 9/2014 | |
| EP | 2777529 | A1 | 9/2014 | |
| EP | 2777530 | A1 | 9/2014 | |
| EP | 2777532 | A2 | 9/2014 | |
| EP | 2777535 | A1 | 9/2014 | |
| EP | 2779921 | A2 | 9/2014 | |
| EP | 2932918 | A1 | 10/2015 | |
| EP | 2944275 | A2 | 11/2015 | |
| EP | 2992834 | A1 | 3/2016 | |
| EP | 2992849 | A1 | 3/2016 | |
| EP | 3000408 | A2 | 3/2016 | |
| EP | 3120780 | A2 | 1/2017 | |
| EP | 3135225 | A2 | 3/2017 | |
| EP | 3158947 | A1 | 4/2017 | |
| EP | 3173029 | A1 | 5/2017 | |
| EP | 3205291 | A1 | 8/2017 | |
| EP | 3338703 | A1 | 6/2018 | |
| EP | 2992834 | B1 | 12/2018 | |
| EP | 3498190 | A1 * | 6/2019 | ....... A61B 17/07207 |
| EP | 3756567 | A1 | 12/2020 | |
| FR | 2828952 | B1 | 12/2005 | |
| JP | S5794132 | A | 6/1982 | |
| JP | 2001170069 | A | 6/2001 | |
| JP | 5301166 | B2 | 9/2013 | |
| JP | 2014530653 | A | 11/2014 | |
| JP | 2016508792 | A | 3/2016 | |
| JP | 2016513570 | A | 5/2016 | |
| JP | 2017500146 | A | 1/2017 | |
| JP | 2017513564 | A | 6/2017 | |
| JP | 2017527396 | A | 9/2017 | |
| JP | 6411461 | B2 | 10/2018 | |
| JP | 2019141659 | A | 8/2019 | |
| KR | 20170060064 | A | 5/2017 | |
| SU | 405234 | A1 | 9/1975 | |
| SU | 886900 | A1 | 12/1981 | |
| SU | 1333319 | A2 | 8/1987 | |
| SU | 1442191 | A1 | 12/1988 | |
| SU | 1459659 | A1 | 2/1989 | |
| WO | WO-8602254 | A1 | 4/1986 | |
| WO | WO-9005489 | A1 | 5/1990 | |
| WO | WO-9734533 | A1 | 9/1997 | |
| WO | WO-03094743 | A1 | 11/2003 | |
| WO | WO-03094746 | A1 | 11/2003 | |
| WO | WO-03094747 | A1 | 11/2003 | |
| WO | WO-2004020859 | A1 | 3/2004 | |
| WO | WO-2009112802 | A1 | 9/2009 | |
| WO | WO-2012142872 | A1 | 10/2012 | |
| WO | WO-2014106275 | A1 | 7/2014 | |
| WO | WO-2016073538 | A1 | 5/2016 | |
| WO | WO-2017026141 | A1 | 2/2017 | |
| WO | WO-2017034803 | A2 | 3/2017 | |
| WO | WO-2017156070 | A1 | 9/2017 | |
| WO | WO-2017214243 | A1 | 12/2017 | |
| WO | WO-2018005750 | A1 | 1/2018 | |
| WO | WO-2018071497 | A1 | 4/2018 | |
| WO | WO-2018118402 | A1 | 6/2018 | |
| WO | WO-2019090047 | A1 | 5/2019 | |
| WO | WO-2020081960 | A1 | 4/2020 | |
| WO | WO-2020131685 | A1 | 6/2020 | |

(56) References Cited

FOREIGN PATENT DOCUMENTS

| | | |
|---|---|---|
| WO | WO-2020131692 A1 | 6/2020 |
| WO | WO-2022150215 A1 | 7/2022 |
| WO | WO-2022200951 A1 | 9/2022 |

OTHER PUBLICATIONS

Anonymous: "Slip Joint Pliers—Wikipedia," Sep. 2017, 1 Pages. Retrieved from internet URL:https://en.wikipedia.org/w/index.php?tilte=split_joint_pliers&oldid=801407143.
Extended European Search Report for Application No. EP19757451.0, mailed on May 19, 2022, 16 pages.
Extended European Search Report for Application No. EP19898247.2, mailed on Jan. 10, 2023, 12 pages.
Extended European Search Report for Application No. EP19900059.7, mailed on Dec. 5, 2022, 10 pages.
Extended European Search Report for Application No. EP20790773.4, mailed on Nov. 29, 2022, 09 pages.
Extended European Search Report for Application No. EP20815112.6, mailed on Jan. 5, 2023, 11 pages.
Extended European Search Report for Application No. EP20875978.7, mailed on Jan. 31, 2024, 26 pages.
Extended European Search Report for Application No. EP24155564.8, mailed on Jul. 8, 2024, 12 pages.
Burstein M.D., "8 MM Sureform 30 Staplers and Reloads," Sages, Jun. 2022, 1 Page. Retrieved from internet URL: https://www.accessdata.fda.gov/cdrh_docs/pdf21/K211997.pdf.
Jaggi A., "8 mm SureForm 30 Curved-Tip Stapler, 8 mm SureForm 30 Stapler, SureForm 30 Reloads," U.S Food & Drug Administration, Dec. 2021, 11 pages. Retrieved from the internet URL:https://www.sages.org/publications/tavac/8-mm-sureform-30-staplers-and-reloads/.
Extended European Search Report for Application No. EP18823002.3 mailed on Mar. 5, 2021, 11 pages.
International Search Report and Written Opinion for Application No. PCT/US2018/039912, mailed on Oct. 12, 2018, 15 pages.
European Search Report (Corrected version) for Application No. EP19750317.0, mailed on Mar. 28, 2022, 26 pages.
Field Application Note—Journal Bearings, Retrieved from Wayback Machine URL: https://web.archive.org/web/20100110095051/ http://www.reliabilitydirect.com/appnotes/jb.html, on Mar. 12, 2024, 04 pages.
International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US19/17646, mailed on Apr. 16, 2019, 11 pages.
International Search Report and Written Opinion for Application No. PCT/US2016/059527, mailed on Feb. 16, 2017, 13 pages.
International Search Report and Written Opinion for Application No. PCT/US2019/019501, mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US202 1/065544 mailed Jun. 2, 2022, 21 pages.
International Search Report and Written Opinion for Application No. PCT/US2020/020672, mailed Jun. 29, 2020, 10 pages.
International Search Report and Written Opinion for Application No. PCT/US2020/025655, mailed Jul. 22, 2020, 8 pages.
International Search Report and Written Opinion for Application No. PCT/US2020/033481, mailed Sep. 3, 2020, 22 pages.
International Search Report and Written Opinion for Application No. PCT/US2020/054568, mailed Jan. 29, 2021, 13 pages.
International Search Report and Written Opinion for Application No. PCT/US2021/012284 mailed May 6, 2021,23 pages.
International Search Report and Written Opinion for Application No. PCT/US2021/065308, mailed Apr. 21, 2022. 13 pages.
Nicholson, C., et al., "Plane Bearings," ESC Report, BSA Educational Services Committee, Oct. 1994, vol. 5(1), 02 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Article Name, found online xx/xx/xxxx at amazon.com (store brand base url). Reference dated xx/xx/xxxx. Retrieved from https://web.archive.org/web/20140704001512/http://www.adorama.com/FSSTC10.html.
"Echelon Gripping Surface Technology Reloads," Ethicon, 2023, 1 Page. Retrieved from online URL:[https://web.archive.Org/web/20230328053734/https://www.jnjmedtech.com/en-US/product/ echelon-gripping-surfacetechnology reloads].
"Itoya 3/8" Switch Heavy Duty Disposable Staple Cassettes," Adorama, 2014, 1 page. Retrieved from Online URL: [https://web.archive.0rg/web/20140704001512/http://www.adorama.com/FSSTC10.html].
"Linear Cutter Stapler," Fengh Europe, 2024, 1 Page. Retrieved from Online URL: [https://web.archive.org/web/20240223162323/https://fenghmedical.nl/product/linear-cutter-stapler/].
McKesson Staple Loading Unit, found online Dec. 30, 2025 at https://mms.mckesson.comReference dated Apr. 15, 2021. Retrieved fromhttps://web.archive.Org/web/20210415093906/https://mms.mckesson.com/product/453729/J-J-Healthcare-Systems-6R45B.

* cited by examiner 102
102a
102b
100
106
112
111
110

140

112
111
117
118

123
124
126
127
122

158
159
122
187
188
150
157
155
179b
111
B
153
112

187
111
A
157
188
155
150
179a 112
122
153
158
159

150
170
172
143
182
180
181
192
193
191
190
144
165

170
172
143
171
184
183
180

150
143
180

178
179
165
111
122
112
114
150
143
180

178
179
165
111
122
112

150
143
144
165
111
112
114
122

150
143
144
165
111
112
114
122

150
143
179
165
100

112
122
111
114

140
170
174
142
143
141
150
165
179
122

SURGICAL STAPLING INSTRUMENT

CROSS-REFERENCE TO RELATED APPLICATIONS

The present application is a continuation of U.S. patent application Ser. No. 17/602,272, filed Oct. 7, 2021, which is the U.S. National Stage of International Application No. PCT/US20/25655 filed Mar. 30, 2020, which claims the benefit which claims the benefit of U.S. Provisional Application No. 62/835,086, filed Apr. 17, 2019, the entire disclosure of which is incorporated herein by reference for all purposes.

BACKGROUND

The present disclosure relates to medical instruments and more particularly to tissue clamping instruments for use in surgeries. Even more particularly, the present disclosure relates to a surgical instrument configured to provide for a desired tissue gap without the use of complicated gap-setting mechanisms. The present disclosure further relates to a surgical stapling instrument having a unique mechanism for securing cartridges within a stationary jaw of the surgical stapling instrument.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems increase a surgeon's dexterity when working on an internal surgical site, as well as allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms. A surgical instrument is mounted on each of the robotic arms. Operative communication between master controllers and associated robotic arm and instrument assemblies is typically achieved through a control system. The control system typically includes at least one processor that relays input commands from the master controllers to the associated robotic arm and instrument assemblies and back in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912, 6,758,843, 6,246,200, and 5,800,423, the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. Nos. 6,702,805, 6,676,669, 5,855,583, 5,808,665, 5,445,166, and 5,184,601, the full disclosures of which are incorporated herein by reference in their entirety for all purposes.

During a surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide two or three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions, especially when deployed into restrictive body cavities (e.g., through a cannula to inside the pelvis).

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting devices, including known surgical staplers, have opposing jaws that clamp tissue and an articulated knife to cut the clamped tissue.

Many surgical clamping and cutting instruments include an instrument shaft supporting an end effector to which a replaceable stapler cartridge is mounted. An actuation mechanism articulates the stapler cartridge to deploy staples from the stapler cartridge to staple tissue clamped between the stapler cartridge and an articulable jaw of the end effector.

The use of surgical clamping and cutting instruments to seal tissue may become difficult and present a variety of issues when a user must accommodate tissue of varying sizes, shapes, thicknesses, and toughness. If a surgical clamping and cutting instrument is not suitable for the specific properties of the tissue being sealed, staple formation may be negatively impacted, generally resulting in a higher rate of negative complications. To address this problem, a user must often switch to a different instrument during the surgical procedure, or use complicated tissue gap-setting mechanisms.

Accordingly, further improvements to surgical instruments would be desirable. In general, it would be desirable to have a surgical instrument that is able to provide for various tissue gaps to effectively accommodate tissue of varying size and thickness without having to use complicated gap-setting mechanisms. Additionally, it would be desirable to provide for a mechanism to secure different reloads, each configured to provide for a unique tissue gap, within the stationary jaw of a singular surgical instrument.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In one aspect, the present disclosure relates to a surgical instrument having an elongate shaft and an end effector on a distal end portion of the shaft. The end effector includes a first jaw, and a coupling member configured to receive either a first or second reload and to removably couple either the first or second reload to the end effector. The coupling member is configured to retain the first reload in a closed position relative to the first jaw such that the first jaw and first reload have a first gap therebetween. The coupling member is configured to retain the second reload in a closed position relative to the first jaw such that the first jaw and the second reload have a second gap therebetween, the second gap being greater than the first gap. The instrument is designed to accommodate reloads having different tissue gaps between the first jaw and the reload, thereby allowing an operator to treat tissue of varying sizes, shapes, thicknesses, and toughness with the same surgical instrument.

In certain embodiments, the first and second reloads include a movable jaw configured for coupling to the first jaw of the surgical instrument. In other embodiments, the first and second reloads include a staple cartridge housing a plurality of staples. In still another embodiment, the reloads include a removable jaw that includes a staple cartridge housed therein.

In embodiments, the coupling member may be a channel configured to receive a coupling element on the reload, such as a pin or other suitable coupling member such that the reload is coupled to the end effector when the pin is moved into the channel. In certain embodiments, the coupling member may be configured to receive an engagement structure of the first or second movable jaw.

In embodiments, the surgical instrument may further include an actuator coupled to the end effector. The actuator may be configured to translate the reload, which may be a movable jaw, movable between a first and second closed positions relative to the fixed jaw. The movable jaw may be substantially parallel to the fixed jaw in the first and second closed positions. This embodiment allows the operator to, for example, translate the movable jaw into multiple parallel positions relative to the fixed jaw to provide a selected tissue gap for treating tissue. In certain embodiments, the movable jaw can be moved into the first closed position relatively close to, or in contact with, the fixed jaw for minimizing the instrument diameter as the instrument, for example, is passed through a cannula. The movable jaw can then be moved into the second closed position with a selected tissue gap between the jaws for clamping, stapling and/or sealing tissue between the fixed and movable jaws.

In certain embodiments, the actuator may be a drive member configured to translate distally through the end effector. In embodiments, the first or second movable jaw includes a pin, and the drive member may include a camming surface configured to engage the pin as the drive member is translated through the end effector to move the first or second jaw from the first closed position to the second closed position.

In embodiments, the pin is pivotally coupled to the first or second movable jaw to allow the first or second movable jaw to pivot relative to the pin and the fixed jaw between open and closed positions.

In embodiments, the surgical instrument may further include a locking mechanism coupled to either the shaft or the end effector and configured to lock the first or second jaw in the second closed position. This ensures that that jaws are locked into the second closed position prior to clamping, stapling and/or sealing the tissue. In embodiments, the locking mechanism includes a latch having a first distal surface and a second proximal surface, wherein the first second proximal surface is disposed laterally away from the first distal surface.

In embodiments, the surgical instrument further includes an actuating mechanism for translating the drive member distally through the end effector. The actuating mechanism may include a control device of a robotic surgical system.

In another aspect, the present disclosure relates to a surgical instrument including an elongate shaft and an end effector on a distal end portion of the shaft. The end effector includes a first jaw and a second jaw configured to move relative to each other from an open position to a first closed position. The first and second jaws are substantially parallel to each other in the closed position. The first and second jaws are movable relative to each other between the first closed position, wherein the jaws define a first distance therebetween, and a second closed or expanded closed position, wherein the jaws define a second distance therebetween. The second distance is greater than the first distance and the first and second jaws are substantially parallel to each other in the second closed position. Moving the jaws between the first and second closed positions allows the operator to both minimize the overall instrument profile when desired (e.g., passing through a cannula) and to position the jaws in an optimal position relative to each other to clamp, seal and/or staple tissue therebetween.

In certain embodiments, the second closed position may be adjustable so that the operator can adjust the distance between the first and second jaws, allowing the operator to select an optimal tissue gap for clamping, sealing and/or stapling tissue. In other embodiments, the second closed position is fixed for a particular staple cartridge. In these embodiments, the instrument may be configured to receive other staple cartridges that provide different tissue gaps in the second closed position.

In certain embodiments, the second jaw may be removably coupled to the end effector.

In embodiments, the surgical instrument may further include a staple cartridge coupled to the second jaw and housing a plurality of staples, and a drive member configured to translate distally through the end effector. The drive member may be configured to engage the staples upon distal translation of the drive member through the staple cartridge and move the staples from an interior of the staple cartridge to an exterior of the staple cartridge.

In embodiments, the end effector defines a longitudinal axis, and wherein the first and second jaws define a gap therebetween in the extended position, wherein the gap extends substantially along the longitudinal axis between the first and second jaws. In embodiments, the surgical instrument further includes an actuator coupled to the end effector, the actuator being configured to move the jaws between the closed and extended positions. In embodiments, the actuator includes a drive member configured to translate distally through the end effector.

In embodiments, the second jaw may include a pin and the drive member may include a camming surface. The camming surface may engage the pin as the drive member is translated through the end effector to move the second jaw from the closed position to the extended position.

In embodiments, the pin is pivotally coupled to the second jaw to allow the jaw to pivot relative to the pin and the first jaw between the open and closed positions.

In embodiments, the surgical instrument further includes a channel on the shaft or the end effector for receiving the pin. The channel may extend in a transverse direction to the longitudinal axis of the shaft, wherein the camming surface translates the pin through the channel to move the second jaw form the closed position to the extended position.

In embodiments, the surgical instrument may further include a locking mechanism coupled to the second jaw and configured to lock the second jaw in the extended position.

In embodiments, the locking mechanism may be a latch having a first distal surface and a second proximal surface, wherein the first second proximal surface is disposed laterally away from the first distal surface.

In embodiments, the surgical instrument may further include an actuation mechanism in contact with the drive member and configured to translate the drive member distally through the end effector, and an actuator operatively connected to the actuation mechanism. In embodiments, the actuator may be a control device of a robotic surgical system.

In another aspect, the present disclosure relates to a surgical instrument including an elongate shaft having an end effector, and a first drive member configured to translate distally through a portion of the end effector. The first drive member may include a first flange at a first end thereof and a first engagement structure at a second end thereof. The surgical instrument may further include a reload removably coupled to the end effector and having a secondary drive member including a second flange at a first end thereof and a second engagement structure at a second end thereof. The second engagement structure may be configured to engage the first engagement structure such that the first drive member and the secondary drive member collectively establish a fixed distance between the first flange of the first drive member and the second flange of the secondary drive member. It is advantageous for the first drive member to engage the secondary drive member as the fixed distance between the first flange of the first drive member and the second flange of the secondary drive member determines the tissue gap of the end effector having a given reload installed. In other words, this allows a given surgical instrument to receive various reloads configured to provide for unique tissue gaps in operation.

In embodiments, the first engagement structure is slot and the second engagement structure is a tab configured to be received within the slot.

In embodiments, the end effector may be a first jaw and the reload may be a second jaw, wherein the first flange is configured to translate through a channel in the first jaw of the end effector, and the second flange is configured to translate through a channel in the second jaw. the first and second jaws are movable between an open position and a closed position to grasp tissue between the first and second jaws.

In embodiments, the drive member and the secondary drive member collectively form an I-beam upon engagement of the first engagement structure with the second engagement structure.

In embodiments, the surgical instrument may further include a spring on the stationary jaw, the spring configured to bias the reload towards the open position. In embodiments, the reload includes a staple cartridge and the stationary jaw includes an anvil.

In embodiments, the drive member may further include a distal ramped surface configured to engage a surface of the reload to pivot the reload toward the closed position upon distal translation of the drive member.

In embodiments, the surgical instrument may be a manually activated surgical instrument, an electro-mechanically powered instrument, or a robotic surgical instrument.

In another aspect, the present disclosure relates to a surgical instrument including a stationary jaw configured to receive a reload having proximal and distal pins. The stationary jaw includes a proximal slot for receiving the proximal pin and a distal slot for receiving the distal pin, wherein movement of the distal pin in the distal slot pivots the reload relative to the stationary jaw between an open position and a closed position. The surgical instrument may further include a latch movable to first retaining position and a second locking position, the proximal pin being movably retained within the proximal slot when the latch is in the first retaining position.

In embodiments, the latch is biased towards the second locking position. In embodiments, the end effector may further include a latch release configured for manual activation to move the latch from the second locked position to a proximal position. In embodiments, the latch release may include a series of grooves on an exposed portion of the latch release. In embodiments, the latch abuts a portion of a drive member, the drive member preventing the latch from translating distally.

In embodiments, the reload may include a staple cartridge and the stationary jaw includes an anvil.

In yet another aspect, the present disclosure relates to a kit including a first reload configured for removable coupling to a surgical instrument. The kit may further include first drive member configured to translate through the reload and having a body with a first height, and a second reload configured for removably coupling to a surgical instrument and including a second drive member configured to translate through the reload and having body with a second height that is greater than the height of the body of the first drive member.

In embodiments, the first and second drive members each include an engagement structure configured for engaging an actuator on the surgical instrument for translating the first and second drive members through the first and second reloads.

In embodiments, each reload includes a staple cartridge.

In embodiments, the first and second drive members may each include a shoe at a first end thereof, and an engagement structure at a second end thereof, the body extending between the shoe and the engagement structure. A height of the body may determine a tissue gap between the reload and a stationary jaw onto which the reload is installed.

In yet another aspect, the present disclosure relates to a method for treating tissue. The method includes installing a reload onto an end effector of a surgical instrument such that the reload is pivotally coupled to a first jaw on the end effector between open and closed positions, the reload and the first jaw may define a first distance therebetween in the closed position, and translating the reload in a substantially perpendicular direction relative to the first jaw to define a second distance therebetween.

In embodiments, the method may further include advancing a drive member in a distal direction through the end effector, the drive member causing the reload to move in the substantially perpendicular direction.

In embodiments, the method may further include engaging a pin on the reload with a camming surface of the drive member as the drive member is advanced distally through the end effector.

In embodiments, the method may further include locking the reload in position with the second distance between the reload and the first jaw.

In embodiments, the method may further include engaging a secondary drive member on the reload with the drive member to form an I-beam as the drive member is advanced distally through the end effector.

In embodiments, the method may further include installing a second reload onto the end effector of the surgical instrument and translating the second reload in the substantially perpendicular direction relative to the first jaw to define a third distance therefore, wherein the third distance is greater than the second distance.

In yet another aspect, the present disclosure relates to a kit including a surgical instrument having an elongate shaft and an end effector including a first jaw. A first staple cartridge may be removably couplable to the end effector and housing a plurality of staples, wherein the first staple cartridge is configured to move between open and closed positions relative to the first jaw. The first jaw and the first staple cartridge may be separated by a first distance in the closed position. The kit may further include a second staple cartridge removably couplable to the end effector and housing a plurality of staples, wherein the second staple cartridge is configured to move between open and closed positions relative to the first jaw. The first jaw and the second staple cartridge may be separated by a second distance in the closed position, the second distance being greater than the first distance.

In embodiments, the first and second staple cartridges are substantially parallel to the first jaw in the closed position.

BRIEF DESCRIPTION OF THE DRAWINGS

The above and other aspects, features, and advantages of the present surgical instruments will become more apparent in light of the following detailed description when taken in conjunction with the accompanying drawings in which.

DETAILED DESCRIPTION

Particular embodiments of the present surgical instruments are described hereinbelow with reference to the accompanying drawings; however, it is to be understood that the disclosed embodiments are merely exemplary of the disclosure and that the present surgical instruments may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail.

While the following disclosure is presented with respect to a surgical instrument configured to staple tissue, it should be understood that certain features of the presently described surgical instruments may be readily adapted for use in any type of surgical clamping, cutting, or sealing instruments. For example, features of the present surgical instruments may be employed to set a tissue gap for treating tissue with electrosurgical energy (e.g., cutting, sealing, ablating, etc.) rather than stapling. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1:
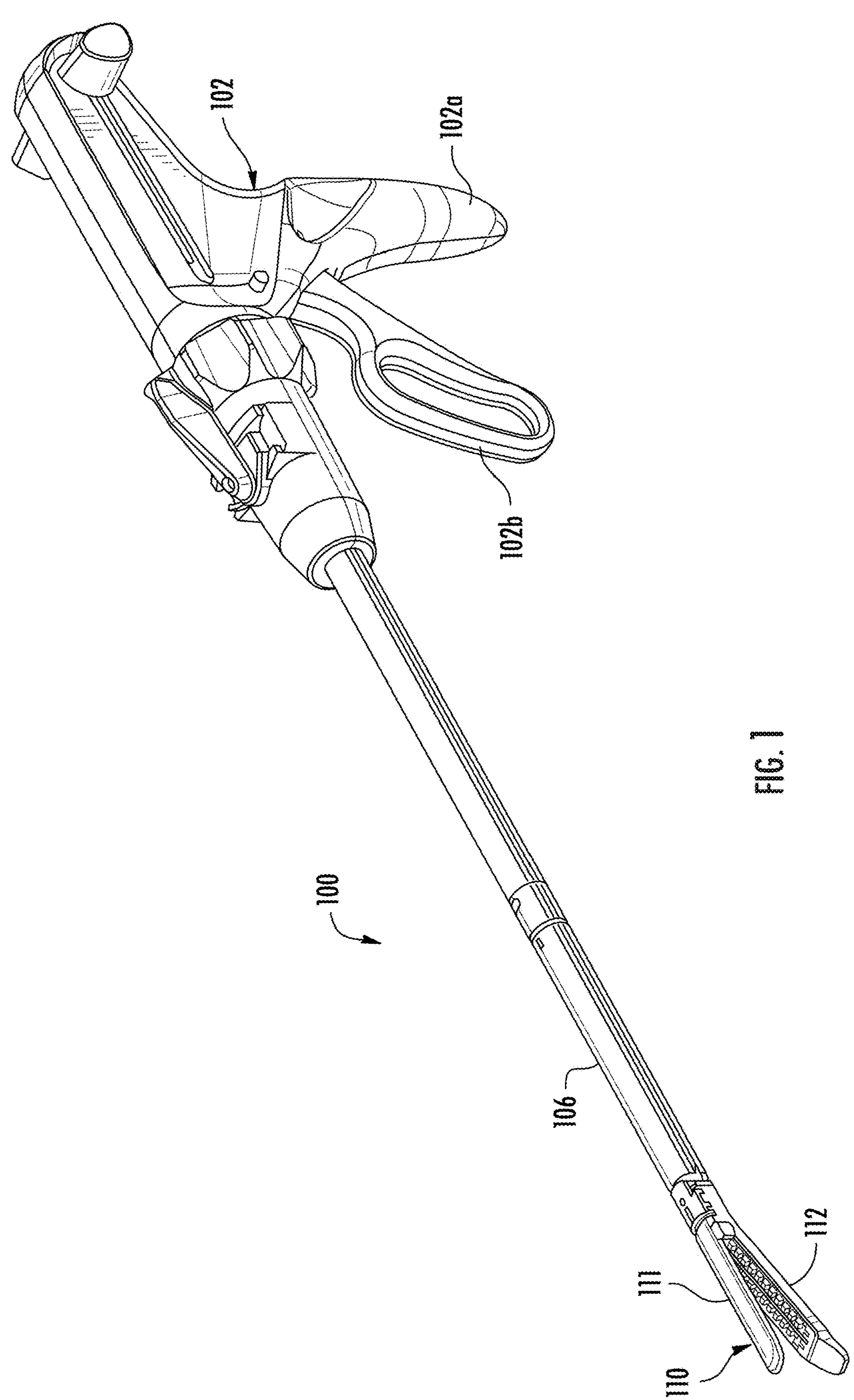
FIG. 1 is a perspective view of an illustrative surgical instrument in accordance with the present disclosure.

FIG. 1 is a perspective view of an illustrative surgical instrument 100 in accordance with embodiments of the present disclosure having a handle assembly 102, and an end effector 110 mounted on an elongated shaft 106 of the surgical stapling instrument 100. End effector 110 includes a stationary jaw 111 and a removable second jaw 112, sometimes referred to herein as reload 112, that is movable relative to stationary jaw 111 from an open position toward a closed position to grasp tissue. In a fully closed position, jaws 111 and 112 are separated by a distance referred to herein as a tissue gap. In the present instruments, the tissue gap is determined by first and second drive members as will be described in detail below. The term "reload" as used in the present disclosure refers to a removable portion of end effector 110 of surgical instrument 100 that may be installed onto end effector 110, used during a procedure, and then removed from end effector 110. The reload may be exchanged with other reloads prior to, during, or after the surgical procedure. The term "reload" may refer to a removable jaw, a staple cartridge or a removable jaw that houses a staple cartridge. While certain embodiments described herein may include a reload 112 that is a removable jaw including a stapler cartridge for use with a surgical stapling instrument, it should be understood that reloads in accordance with this disclosure may be a variety of removable jaws configured for use with various surgical instruments in which varying the tissue gap is desirable, such as, for example, a surgical sealing instrument configured to treat tissue with electrosurgical energy (e.g., cutting, sealing, ablating, etc.).

Handle assembly 102 includes a stationary handle **102*a* and a moveable handle 102*b* which serves as an actuator for surgical instrument 100. In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S Pub. No. 2014/0183244A1, the entire disclosure of which is incorporated by reference herein for all purposes. The input couplers are drivingly coupled with one or more input members (not shown) that are disposed within the instrument shaft 106 and end effector 110**. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety for all purposes. Further details of known input couplers and surgical systems are described, for example, in U.S. Pat. Nos. 8,597,280, 7,048,745, and 10,016,244. Each of these patents is hereby incorporated by reference in its entirety for all purposes.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties for all purposes. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 2:
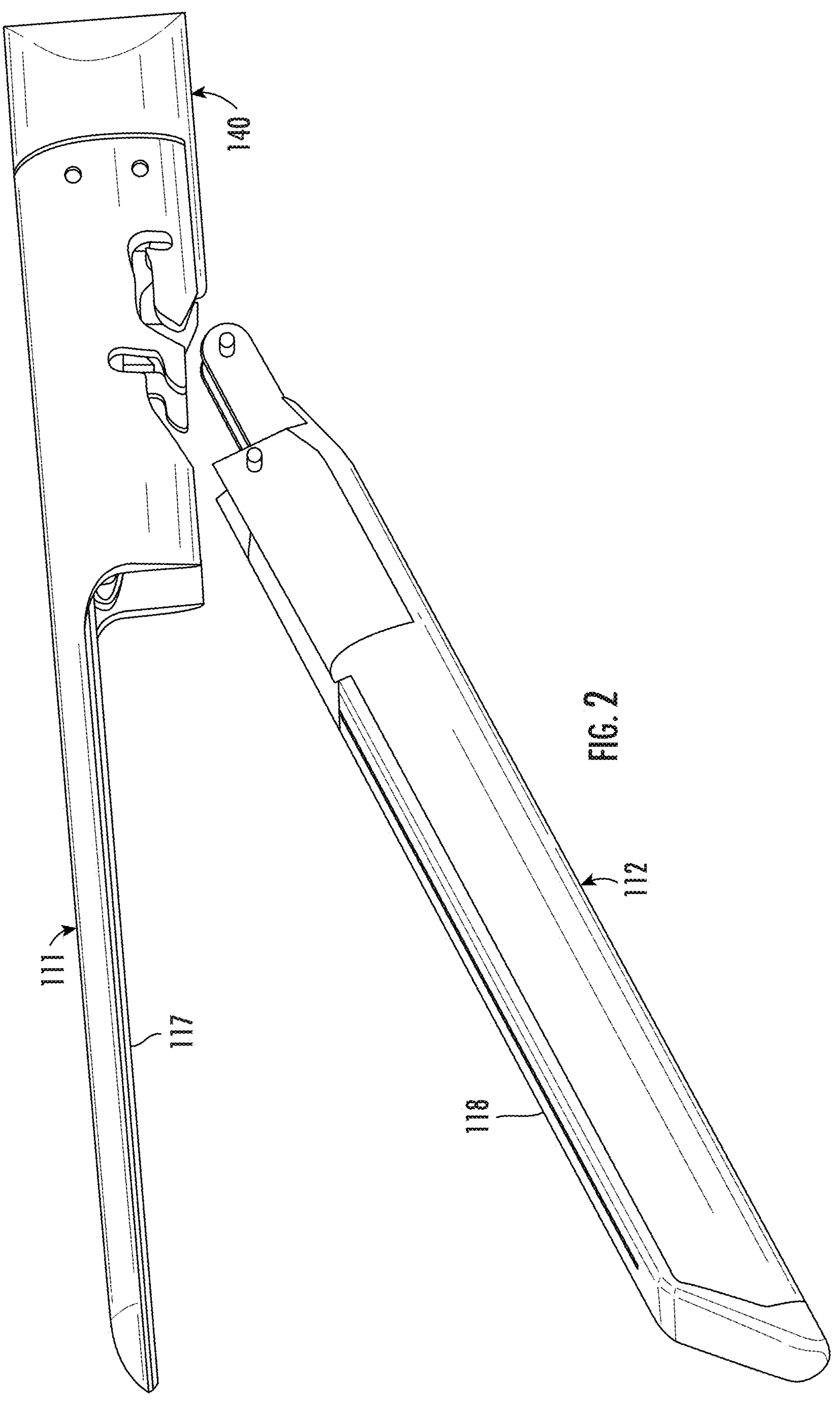
FIG. 2 is a perspective view of a stationary jaw and a reload of an illustrative surgical instrument in accordance with the present disclosure.

FIG. 2 is a perspective view of the jaws of surgical instrument 100 including stationary jaw 111, removable jaw 112 and a clevis 140 for mounting jaws 111, 112 to instrument 100. Stationary jaw 111 is configured to receive removable jaw 112. Once removable jaw 112 is received by and secured to jaw 111, tissue may be grasped between tissue contacting surfaces 117 of jaw 111 and tissue contacting surfaces 118 of removable jaw 112 as it moves and pivots towards stationary jaw 111.

Figure 3:
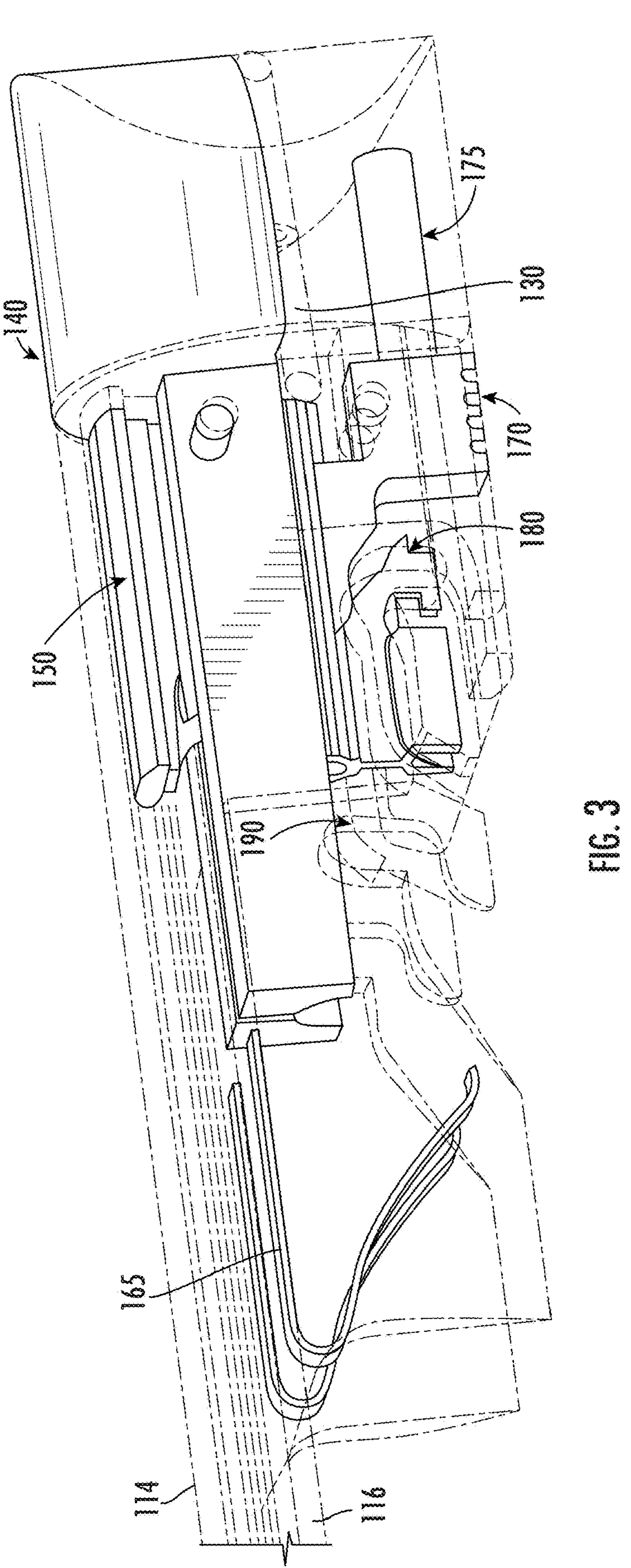
FIG. 3 is a partial perspective view of a stationary jaw of an illustrative surgical instrument in accordance with the present disclosure.

FIG. 3 is a perspective view of a proximal portion of stationary jaw 111 which includes an anvil 114, a drive member 150, an anvil spring 165, a latch 170, a latch spring 175, a proximal slot 180, and a distal slot 190. As those skilled in the art will appreciate, stationary jaw 111 is symmetrical having corresponding structure on either side thereof.

Stationary jaw 111 may include coupling members for receiving removable jaw 112. In embodiments, proximal slots 180 and distal slots 190 of stationary jaw 111 are configured to receive pins of removable jaw 112 such that removable jaw 112 may be installed on end effector 110 of surgical instrument 100. The design of stationary jaw 111 of surgical instrument 100 is such that stationary jaw 111 may receive and support various reloads 112 each configured to provide a particular tissue gap between stationary and removable jaws 111, 112 for surgical instrument 100 upon installation. Anvil spring 165 has one end secured to anvil 114, and another end that is free to contract upon contact with a cartridge during installation of a fresh reload. This will allow for stationary jaw 111 and movable jaw 112 to remain in a passively open position except when the bias over spring 165 is overcome during closing of the jaws 111,112 for actuation or translation through a cannula. The details of the opening and closing of jaws 111,112 will be further described below.

Figures 5, 6:
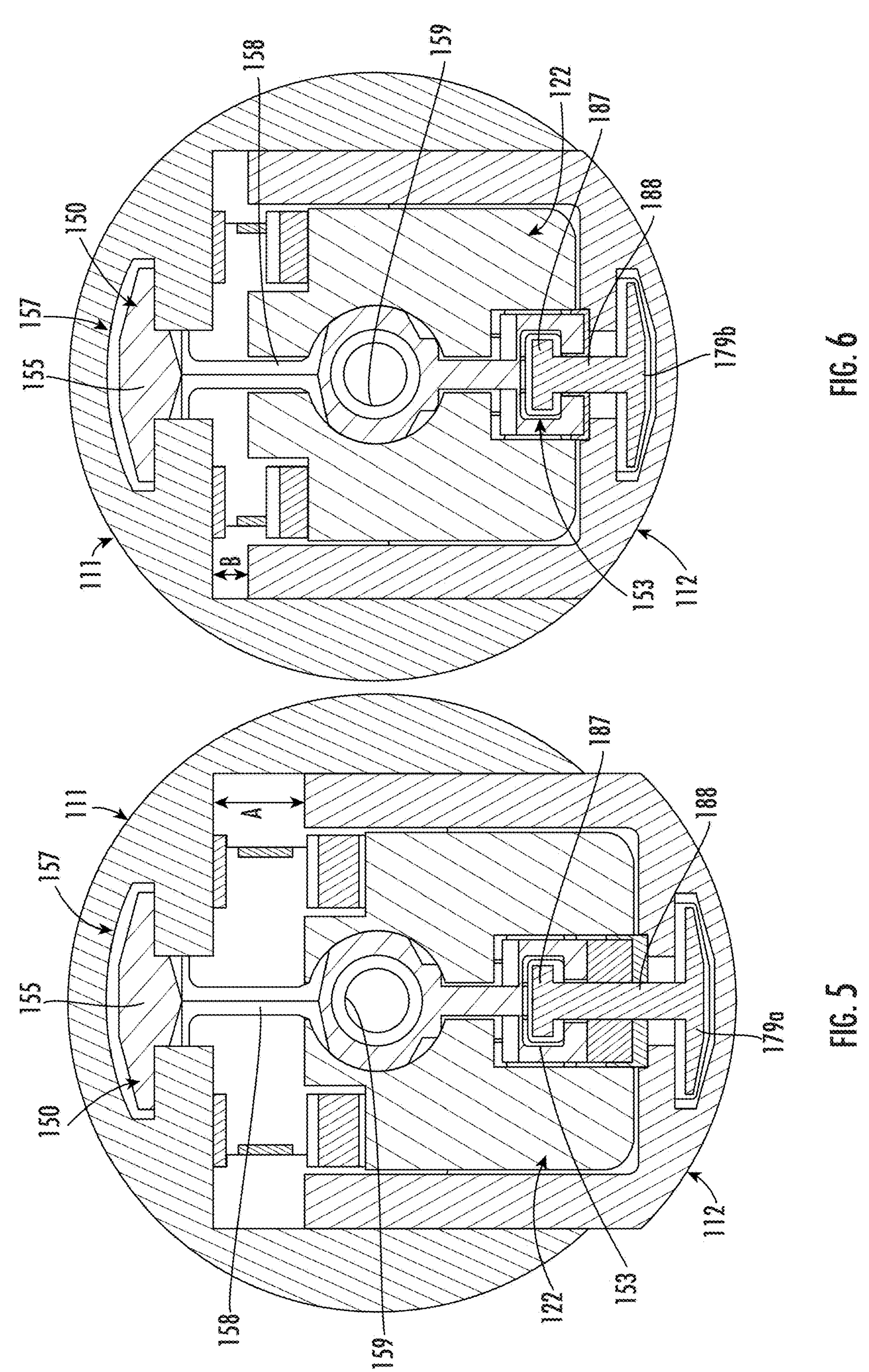
FIGS. 5-6 are cross-sectional views of a portion of the end effector of the surgical instrument of FIG. 1 each having a unique reload and tissue gap.

As best shown in FIGS. 5 and 6, drive member 150 contains a flange (sometimes referred to hereinafter as a shoe) 155 that travels within a channel 157 in stationary jaw 111. A center bore 159 of drive member 150 is configured to receive an actuation mechanism such as a drive rod 130 that is operably connected to moveable handle 102*b* such that movement of movable handle 102*b* towards stationary handle 102*a* causes drive member 150 to translate distally through end effector 110 and movement of movable handle 102*b* away from stationary handle 102*a* causes drive member 150 to retract proximally through end effector 110. In embodiments, the actuation mechanism may include a series of cables or other actuators as discussed previously in connection with FIG. 1. Body 158 connects shoe 155 and bore 159. Lower portion of drive member 150 contains a slot 153 (see FIG. 14) and a number of cam surfaces for engaging portions of jaw 112. Slot 153 functions as an engagement structure and is configured to engage a secondary engagement structure on jaw 112 (e.g., proximal tab 178 of secondary drive member 179), as will be shown below in connection with FIG. 14.

Figure 4:
FIG. 4 is a perspective view of a reload of an illustrative surgical instrument in accordance with the present disclosure.
Figure 4:
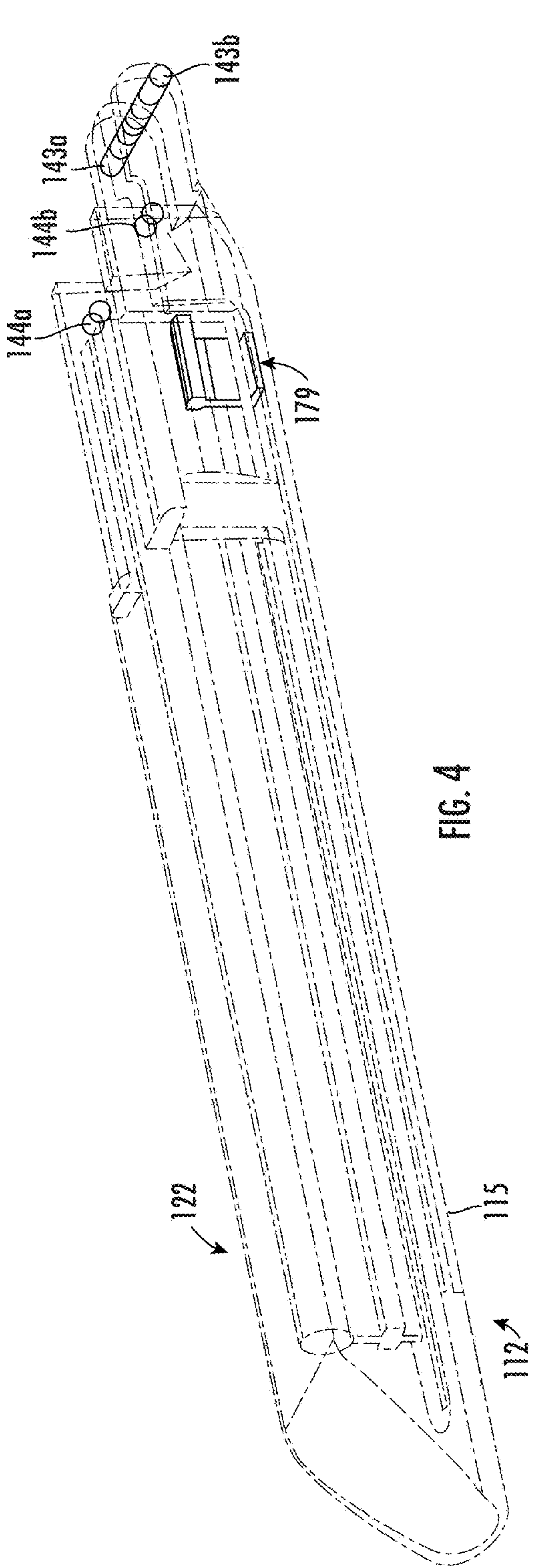

FIG. 4 is a perspective view of an illustrative removable jaw 112 including a staple cartridge 122, secondary drive member 179, channel 115, pivot pins 143*a,b* and hard stop pins 144*a,b*. Removable jaw 112 is configured to be received by stationary jaw 111 such that upon installation, removable jaw 112 provides a movable jaw pivotable from an open position to a closed position relative to stationary jaw 111 to grasp tissue. Stapling cartridge 122 is contained in channel 115 of removable jaw 112. As removable jaw 112 pivots from an open position, stationary jaw 111 and removable jaw 112 cooperate to clamp tissue such that cartridge 122 and anvil 114 are in close cooperative alignment.

Figure 4A:
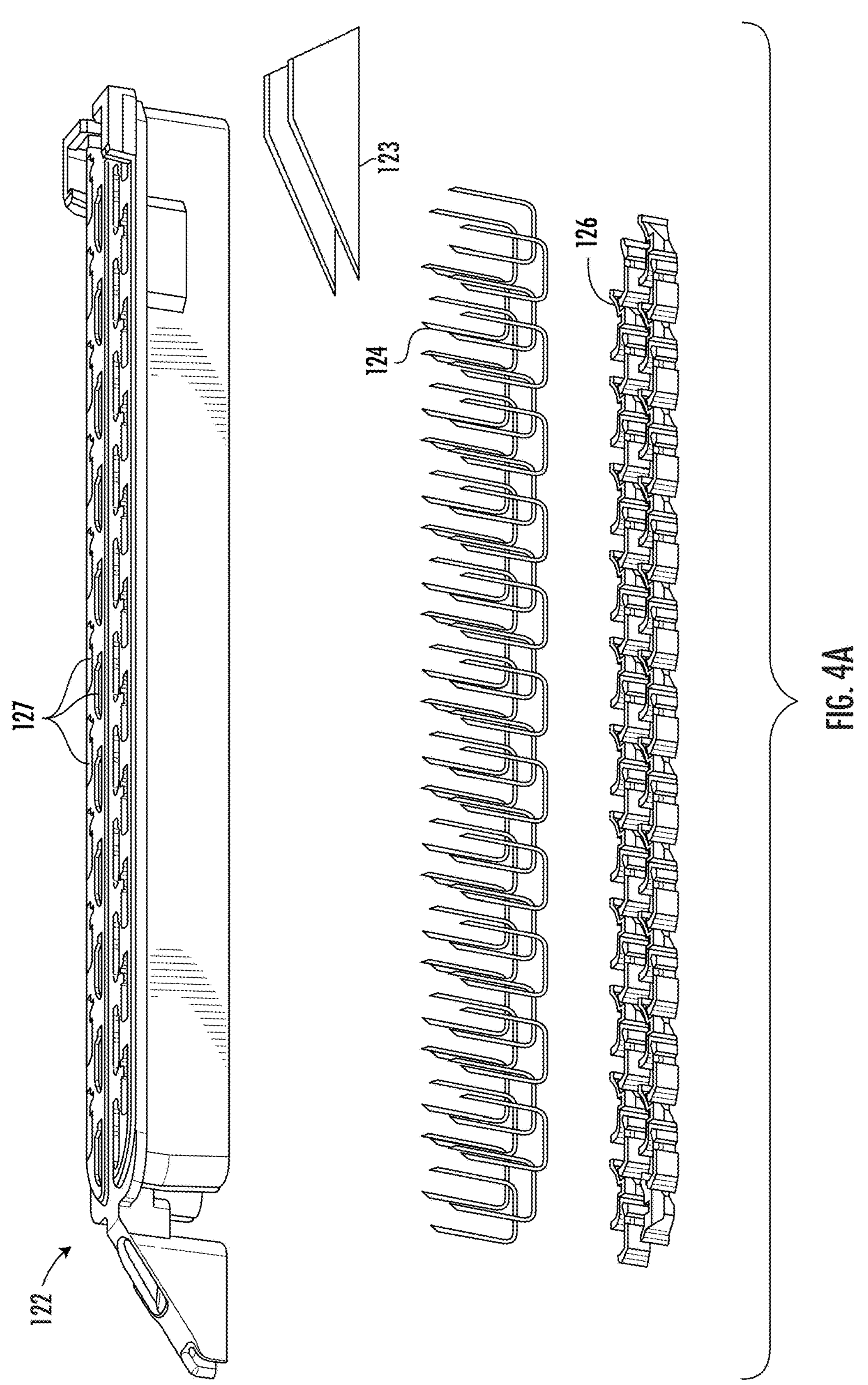
FIG. 4A is an exploded view of a reload of an illustrative surgical instrument in accordance with the present disclosure.

FIG. 4*a* shows that cartridge 122 may include a plurality of staples 124 supported on corresponding staple drivers 126 provided within respective staple apertures 127 formed in cartridge 122. Cartridge 122 also may include a shuttle 123 having an inclined distal portion 125 that, upon distal movement, sequentially acts on staple drivers 126, camming them upwardly thereby moving staples 124 into deforming contact with anvil 114. A knife (not shown) may be configured to translate distally through end effector 110 to sever clamped, stapled tissue. The knife may be a sharpened edge formed on drive member 150. Cartridge 122 may be removably received within removable jaw 112 or, in single use embodiments, may be permanently secured within removable jaw 112.

Reload 112 also includes secondary drive member 179. As best seen in FIGS. 5 and 6, secondary drive member 179 includes a flange (sometimes referred to hereinafter as a shoe) 187 that travels in a channel 131 in jaw 112 and a body 188 extending from shoe 187 and terminating in a proximal tab 178 (see FIG. 14) which functions as an engagement structure and is configured to engage a slot 153 of drive member 150. Since the height of drive member 150 (which is not part of the replaceable reload) is constant, choosing a reload with a secondary drive member 179 having a body 188 of a particular height (which may be different in different reloads) may be used to adjust the size of the tissue gap between jaws 111, 112 when the jaws are in the extended closed position relative to each other (as discussed below).

A plurality of reloads 112 may be provided in a kit, with different reloads including secondary drive members 179 having bodies 188 of different sizes (compare FIGS. 5 and 6) to define different tissue gaps between the removable jaw 112 and anvil 114 of stationary jaw 111. The tissue gap of surgical instrument 100 is determined by the height of secondary drive member 179. In embodiments, when engaged together, drive member 150 and secondary drive member 179 collectively form an I-beam or E-beam, as will be further described below. Although slot 153 and proximal tab 178 are shown as the engagement structure to connect drive member 150 and secondary drive member 179, it should be understood that other suitable engagement structures (e.g., other interlocking structures) may be employed. For example, the drive member may include a tab and the secondary drive member may include a slot. Those skilled in the art reading this disclosure will readily envision other structural configurations suitable for the engagement structures.

FIGS. 5 and 6 show cross-sectional views of a portion of the end effector of surgical instrument 100 including stationary jaw 111, removable jaw 112, drive member 150, cartridge 122, and secondary drive member 179.

Figures 10A, 10B:
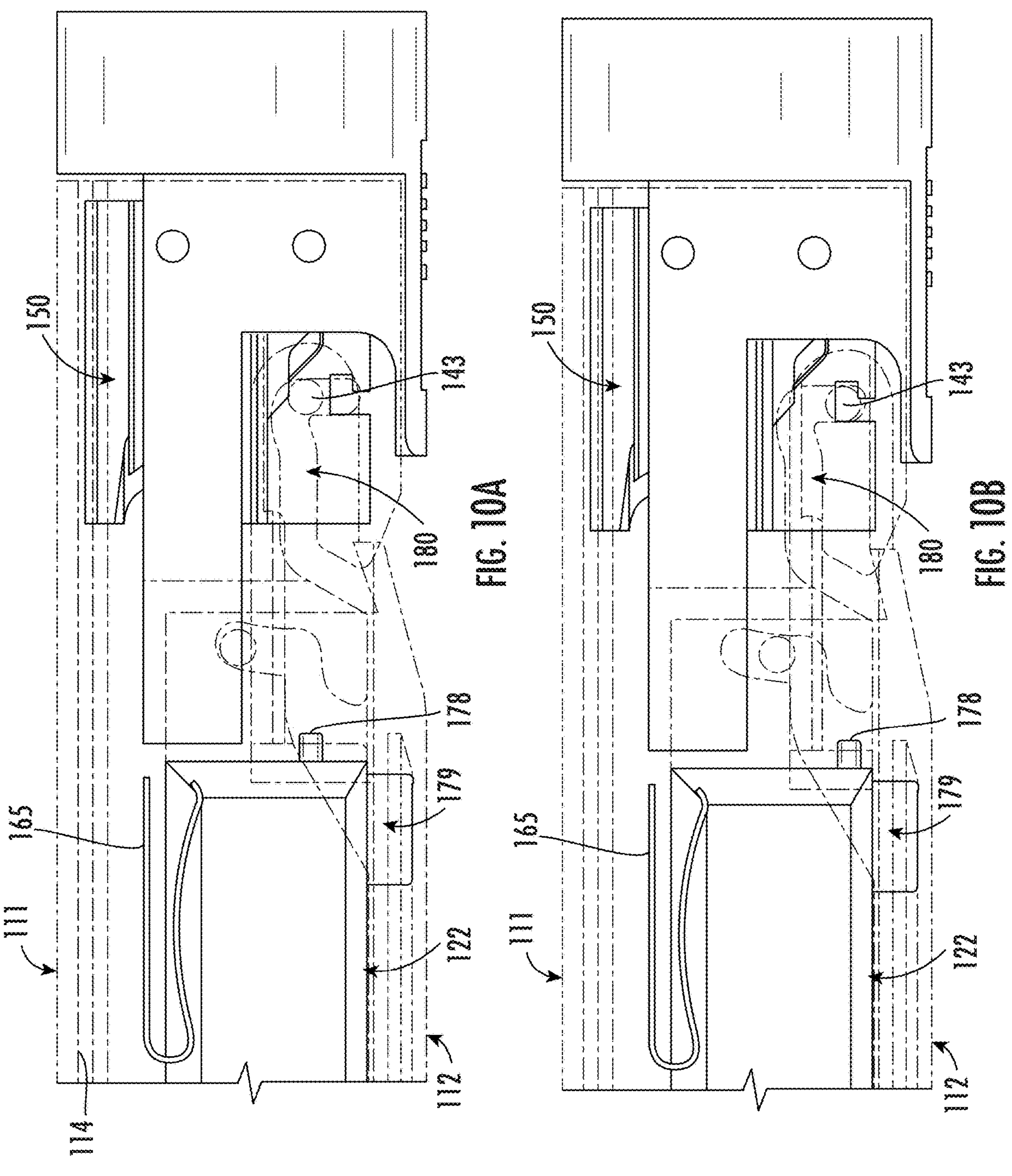
FIG. 10A is a partial perspective view of the end effector of the surgical instrument of FIG. 1 being inserted through a cannula.
FIG. 10B is a partial perspective view the of end effector of the surgical instrument of FIG. 1 being inserted through a cannula.

In FIG. 5, surgical instrument 100 is in an extended closed position in which drive member 150 has begun to translate distally to engage and pick up secondary drive member 179, but has not yet fired staples or severed tissue. As previously noted, choosing a reload with a secondary drive member 179 of a particular overall height may be used to set the desired tissue gap. Removable jaw 112 of surgical instrument 100 contains a secondary drive member 179*a*, having a height configured to set a tissue gap "A". Prior to actuating and firing, as best seen in FIG. 10A below, the removable jaw 112 may be compressed towards stationary jaw 111 to permit the instrument to travel through a cannula. Once the end effector extends out of the cannula, the removable jaw 112 moves away from the stationary jaw 111, ensuring that upon translation of drive member 150 distally, the engagement structure (e.g., slot 153) of the drive member 150 is properly aligned with the engagement structure (e.g., proximal tab 178) of the secondary drive member 179. The amount of movement of the removable jaw 112 away from the stationary jaw 111 to align the engagement structures of the drive member 150 and secondary drive member 179 may vary based on the height of secondary drive member 179.

FIG. 6 shows surgical instrument 100 having a removable jaw 112 including a cartridge 122, and a secondary drive member 179*b* having a shorter overall height in the extended closed position than secondary drive member 179*a* shown in FIG. 5. The shorter height of drive member 179*b* provides for tissue gap "B". One of ordinary skill will appreciate that the tissue gap for surgical instrument 100 in FIG. 6 is thinner than the tissue gap in FIG. 5 as a result of the height of the secondary drive member 179 contained in removable jaw 112.

Figure 7:
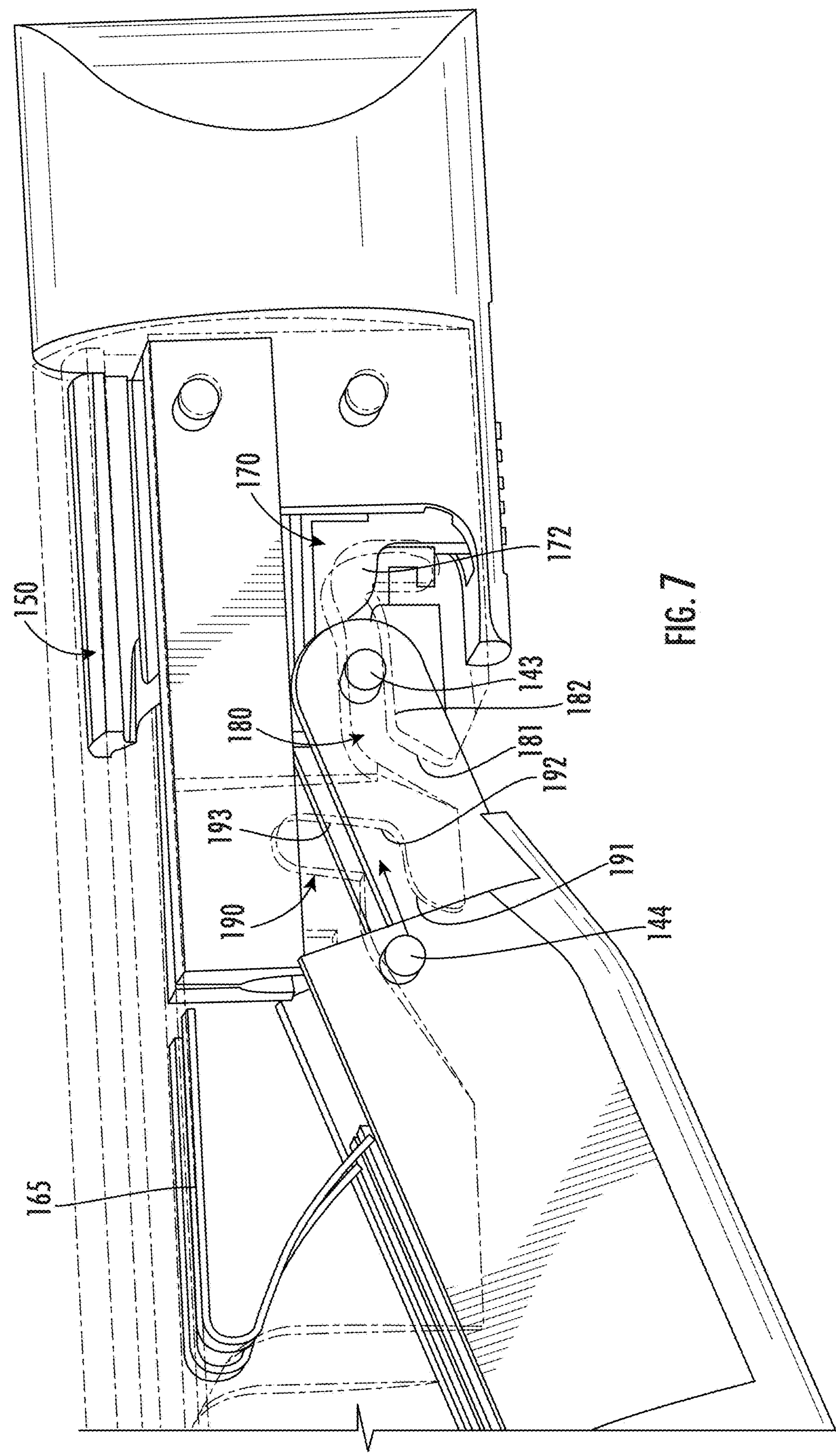
FIG. 7 is a partial perspective view of the end effector of the surgical instrument of FIG. 1 depicting an illustrative reload being installed.
Figure 8:
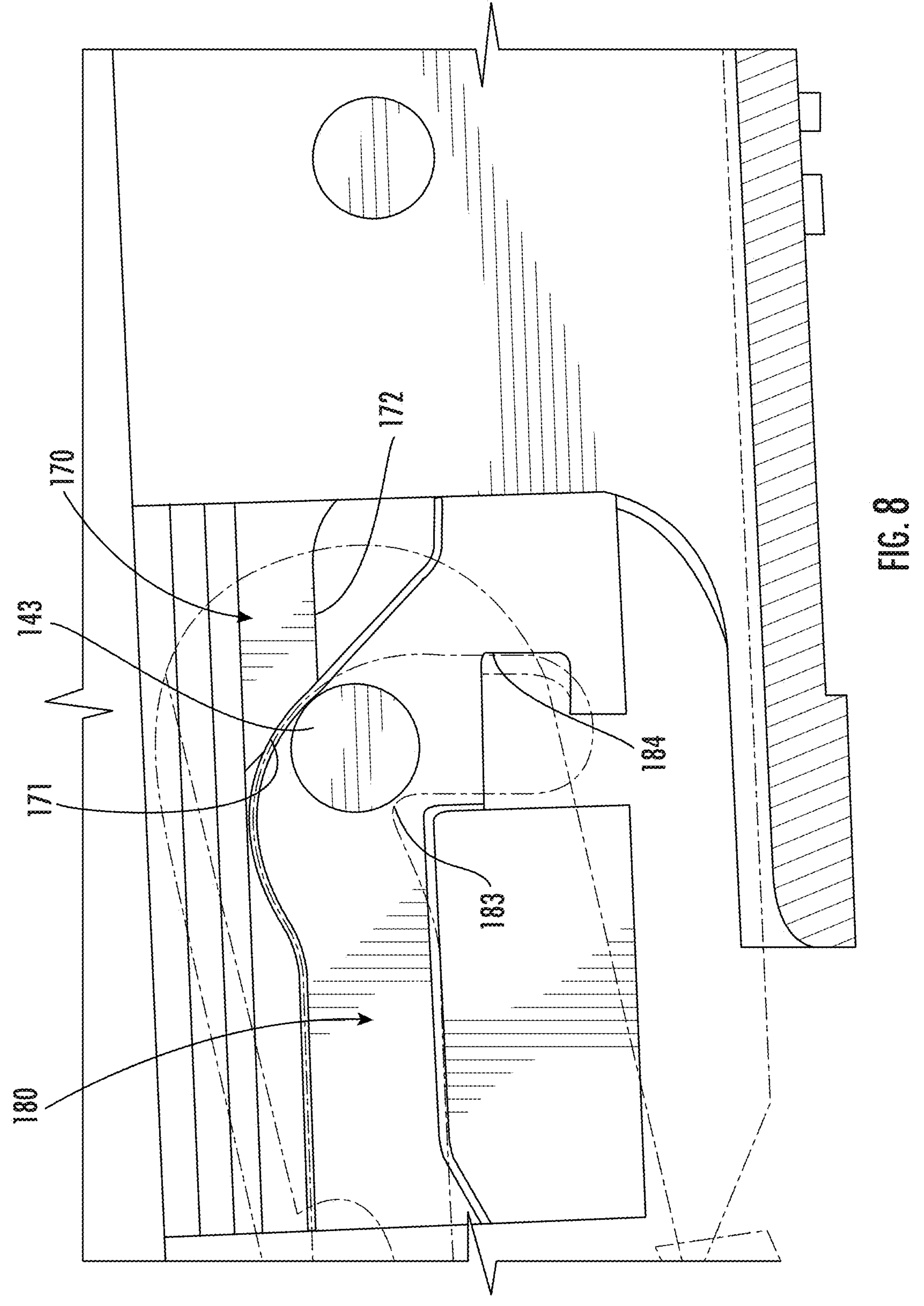
FIG. 8 is a partial perspective view of the end effector of the surgical instrument of FIG. 1 depicting a pin engaging a latch during installation of a reload.
Figure 9:
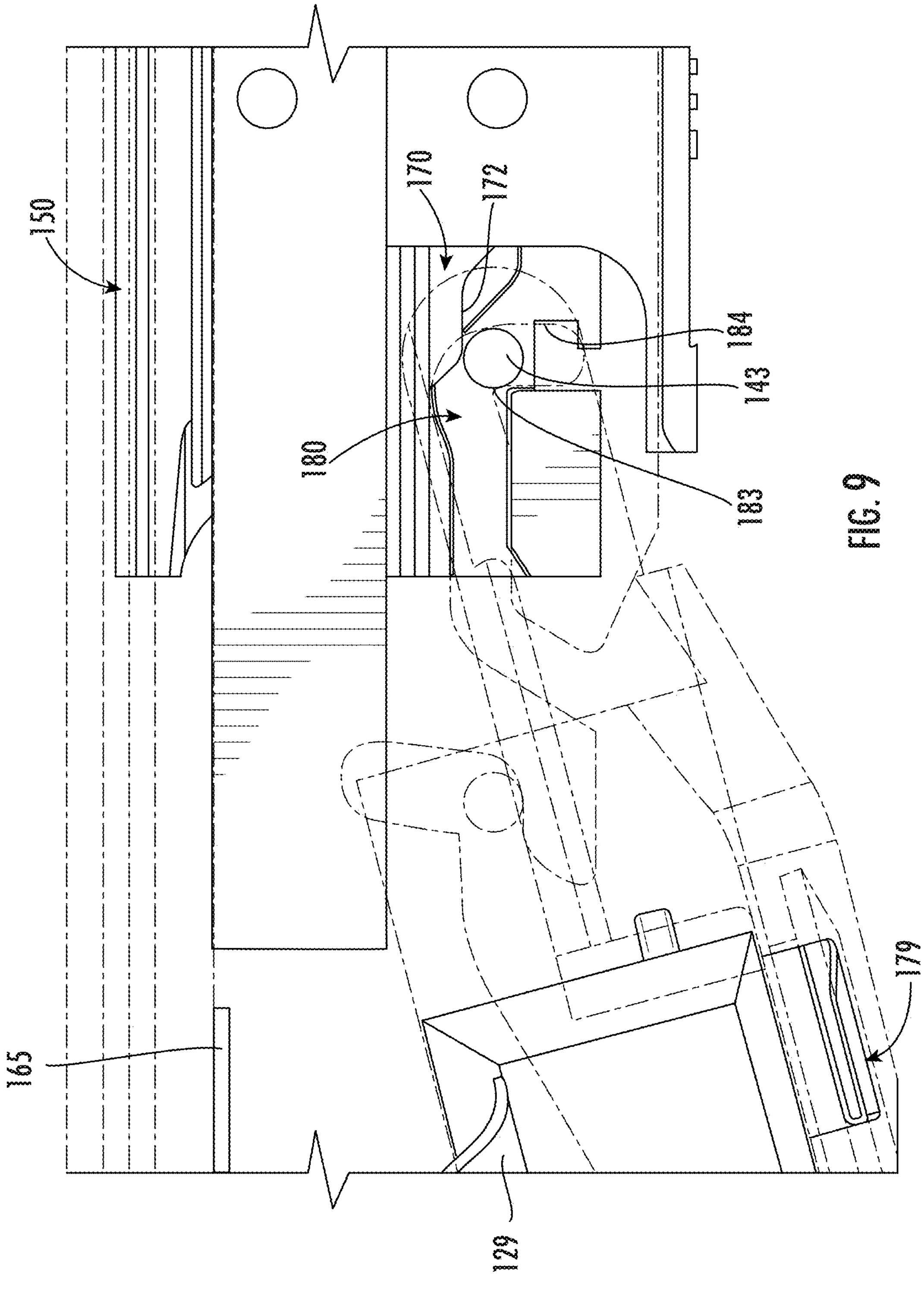
FIG. 9 is a partial perspective view of the end effector of the surgical instrument of FIG. 1 depicting an illustrative reload installed and secured.

FIGS. 7-9 depict the installation of a removable jaw 112 into stationary jaw 111 of surgical instrument 100.

FIGS. 7-9 illustrate the installation of removable jaw 112 onto stationary jaw 111. Removable jaw 112 may be installed manually. As shown in FIG. 7, a user initially guides a pivot pin 143*a,b* and hard stop pins 144*a,b* into proximal slot 180*a,b* and distal slot 190*a,b* respectively. Proximal pin 143 engages distal ramped surface 181 of proximal slot 180 until reaching and riding through a central portion 182 of proximal slot 180. Simultaneously distal pin 144 engages a distal ramped surface 191 of distal slot 190 to urge distal pin 144 proximally towards closing portion 193 of slot 190, where distal pin 144 can no longer move proximally because it is stopped by edge 192 of distal slot 190.

As shown, latch 170 is biased by latch spring 175 (see FIG. 3) towards a distal position designed to retain proximal pin 143 within proximal slot 180, thereby retaining removable jaw 112 in the installed position within stationary jaw 111. Latch spring 175 is received within a bore 197 formed on latch 170. When latch 170 is in the spring-biased distal position, a distal face 171 of latch 170 is substantially aligned with central portion 182 of proximal slot 180 such that distal face 171 obstructs proximal pin 143 after it has traveled through central portion 182 of proximal slot 180.

Referring now to FIG. 8, removable jaw 112 has been pushed further in the proximal direction as it is being installed into stationary jaw 111. Proximal pin 143 has traveled through central portion 182 of proximal slot 180 and is now engaging distal ramped surface 171 of latch 170. As the bias of latch spring 175 is overcome by the manual force applied by a user upon installation, proximal pin 143 slides along distal ramped surface 171 of latch 170, ultimately pushing latch 170 proximally and allowing proximal pin 143 to ride underneath latch 170. At this point, proximal pin 143 may ride below lower surface 172 of latch 170 into a proximal portion 184 of proximal slot 180.

In FIG. 9, proximal pin 143 has cleared lower surface 172 of latch 170. This causes spring 175 to force latch 170 distally to a first retaining position, trapping proximal pin 143 between lower face 172 of latch 170 and an edge 183 of proximal slot 180. The distance between lower surface 172 of latch 170 and edge 183 of proximal slot 180 is less than the diameter of proximal pin 143. In this position, removable jaw 112 is secured to stationary jaw 111, as proximal pin 143 cannot escape the proximal portion 184 of proximal slot 180. Thus, latch 170 is movable to a first retaining position to keep pin 143 movably retained within the proximal slot within proximal slot 180.

Once removable jaw 112 is installed and secured, surgical instrument 100 may be inserted through a cannula towards a surgical site. In embodiments, the height of secondary drive member 179 in a given removable jaw or reload 112 will determine the distance proximal pin 143 moves within proximal portion 184 of proximal slot 180, for example, as the removable jaw 112 is compressed towards anvil 114 in preparation for traveling through a cannula towards a surgical site.

FIGS. 10A and 10B depict surgical instrument 100 with two different reloads or removable jaws both in a first closed position that minimizes the diameter of instrument 100. The first closed position may be suitable, for example, when the instrument travels through a cannula or other percutaneous penetration into a patient. FIG. 10A depicts surgical instrument 100 having a removable jaw 112 configured to provide a relatively thick tissue gap between jaws 111, 112 when the instrument is in a second or "extended" closed position suitable for clamping, sealing and/or stapling tissue (the extended closed position is discussed below and shown in FIGS. 13B and 13C). FIG. 10B depicts surgical instrument 100 having a removable jaw 112 configured to provide for a relatively thin tissue gap in the second or extended closed position. To insert surgical instrument 100 through a cannula once a reload is installed, a user manually overcomes the bias of anvil spring 165 by pushing removable jaw 112 towards the anvil and then inserting the instrument into a cannula while the jaws are at least somewhat closed. Once inserted, the cannula forces surgical instrument 100 to conform to the diameter of the cannula. It should be noted that while in the cannula, the unique tissue gap of removable jaw 112 is not yet activated, as secondary drive member 179 is not engaged with drive member 150 and thus jaw 112 is able to move towards and away from anvil 114. This allows anvil spring 165 to be compressed enough to conform to the smaller diameter of a cannula regardless of the size of the tissue gap removable jaw 112 is configured to provide. One of ordinary skill will appreciate that while within the cannula, proximal pin 143 and distal pin 144 will translate upwards or downwards within their respective slots depending on the amount of compression of removable jaw 112 that is necessary to conform surgical instrument 100 to the diameter of the cannula. This is depicted in FIGS. 11A and 11B respectively.

Figures 11A, 11B:
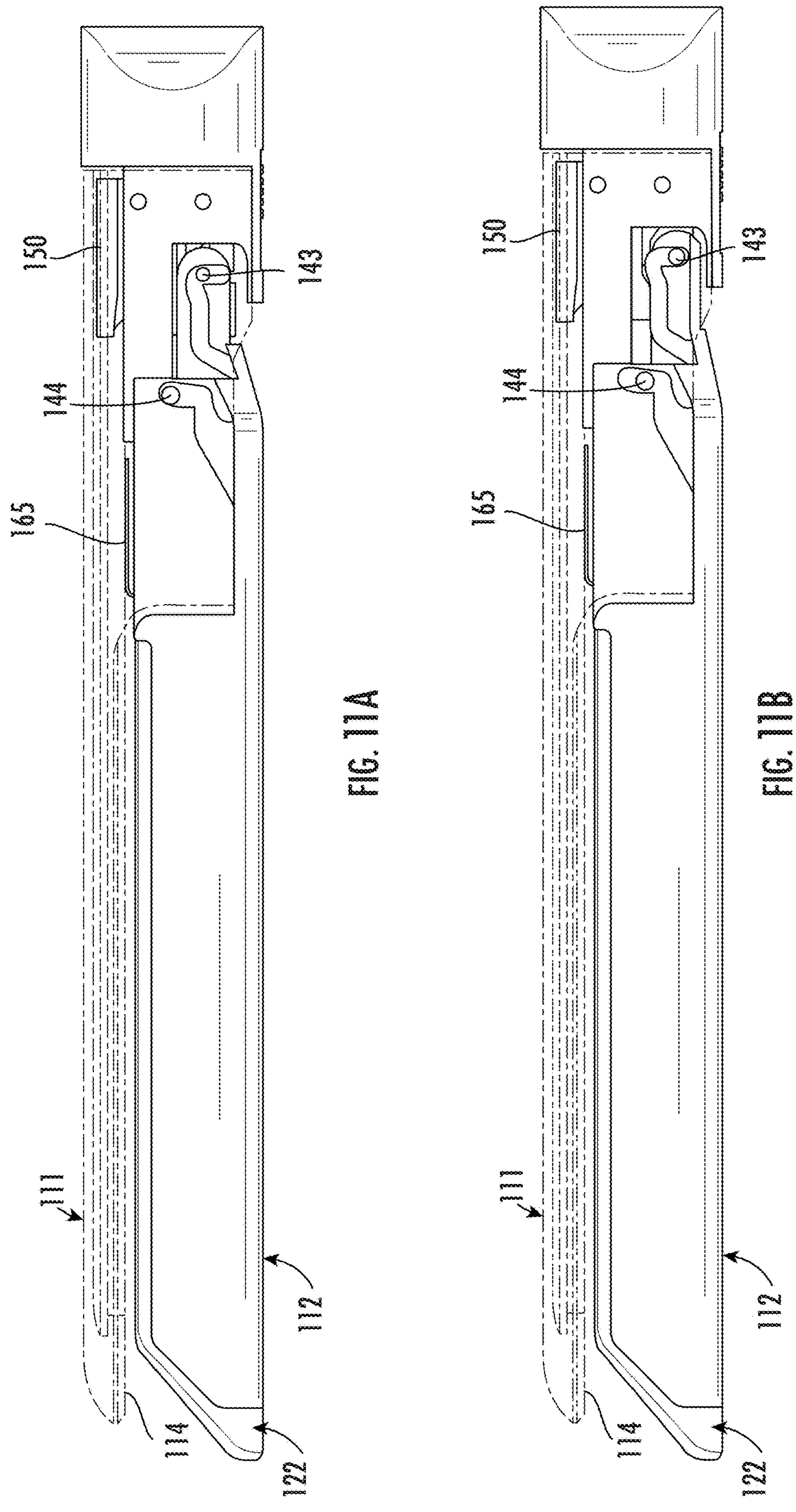
FIG. 11A is a partial perspective view of the end effector of the surgical instrument of FIG. 5 being inserted through a cannula.
FIG. 11B is a partial perspective view of the end effector of a surgical instrument of FIG. 6 being inserted through a cannula.

FIG. 11A depicts the end effector and removable jaw of the embodiment shown in FIG. 5, configured to provide for a first tissue gap, passing through a cannula. FIG. 11B depicts the end effector and removable jaw of the embodiment shown in FIG. 6, configured to provide for a second tissue gap different from the first tissue gap, passing through a cannula. As shown, proximal and distal pins 143, 144 of the two different reloads are in different vertical positions within slots 180, 190 while in the first closed position. This means that pins 143, 144 will travel different distances vertically downward through slots 180, 190 when the reloads are moved into the second or extended closed positions (FIGS. 13B and 13C). Thus, the reloads will be moved away from fixed jaw 111 by different distances when moving them into the second closed positions, creating different tissues gaps therebetween.

Figure 11C:
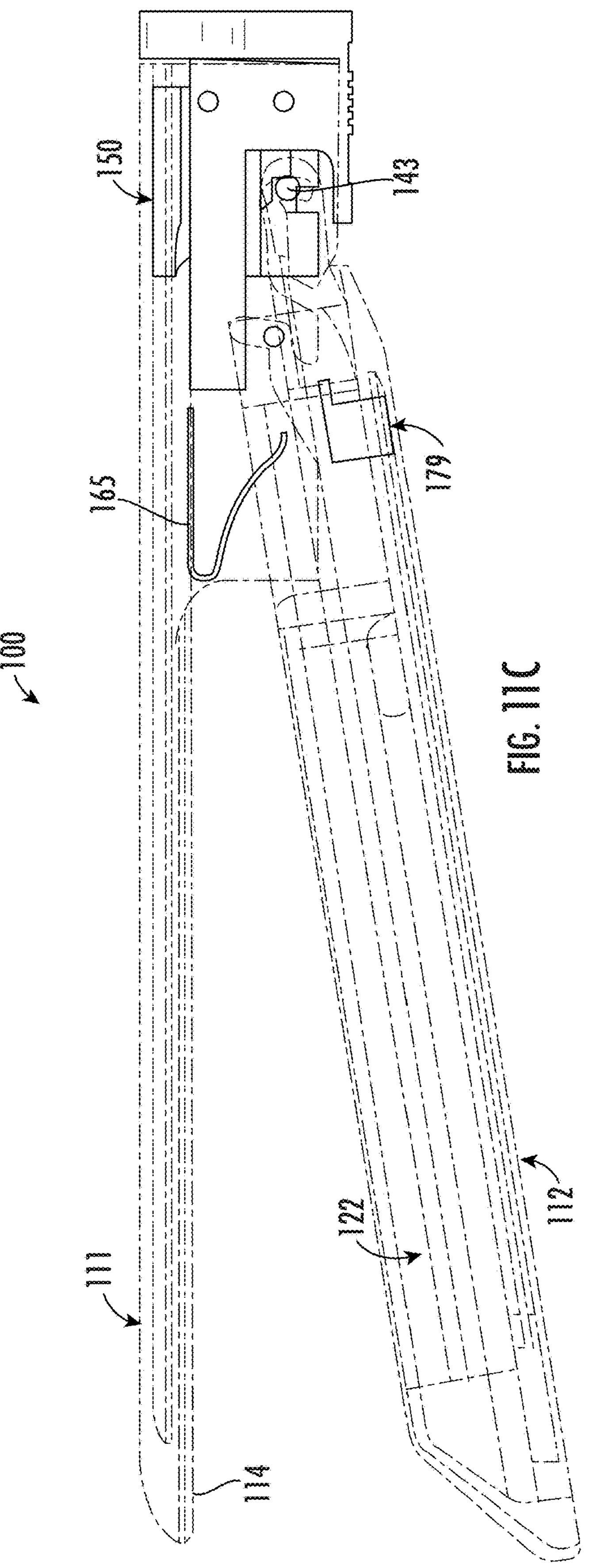
FIG. 11C is a partial perspective view with parts removed of the end effector of the surgical instrument of FIG. 1 in a passively open position after passing through a cannula.

FIG. 11C depicts surgical instrument 100 that has been passively opened by anvil spring 165 after passing through a cannula towards a surgical site. In FIG. 11C, removable jaw 112 remains securely installed within stationary jaw 111, as latch 170 is still trapping proximal pin 143. However, once passing through a cannula, anvil spring 165 continues to bias the jaws of surgical instrument 100 towards the open position. This causes removable jaw 112 to pivot away from stationary jaw 111, ultimately resting in a passively open position.

Figure 12:
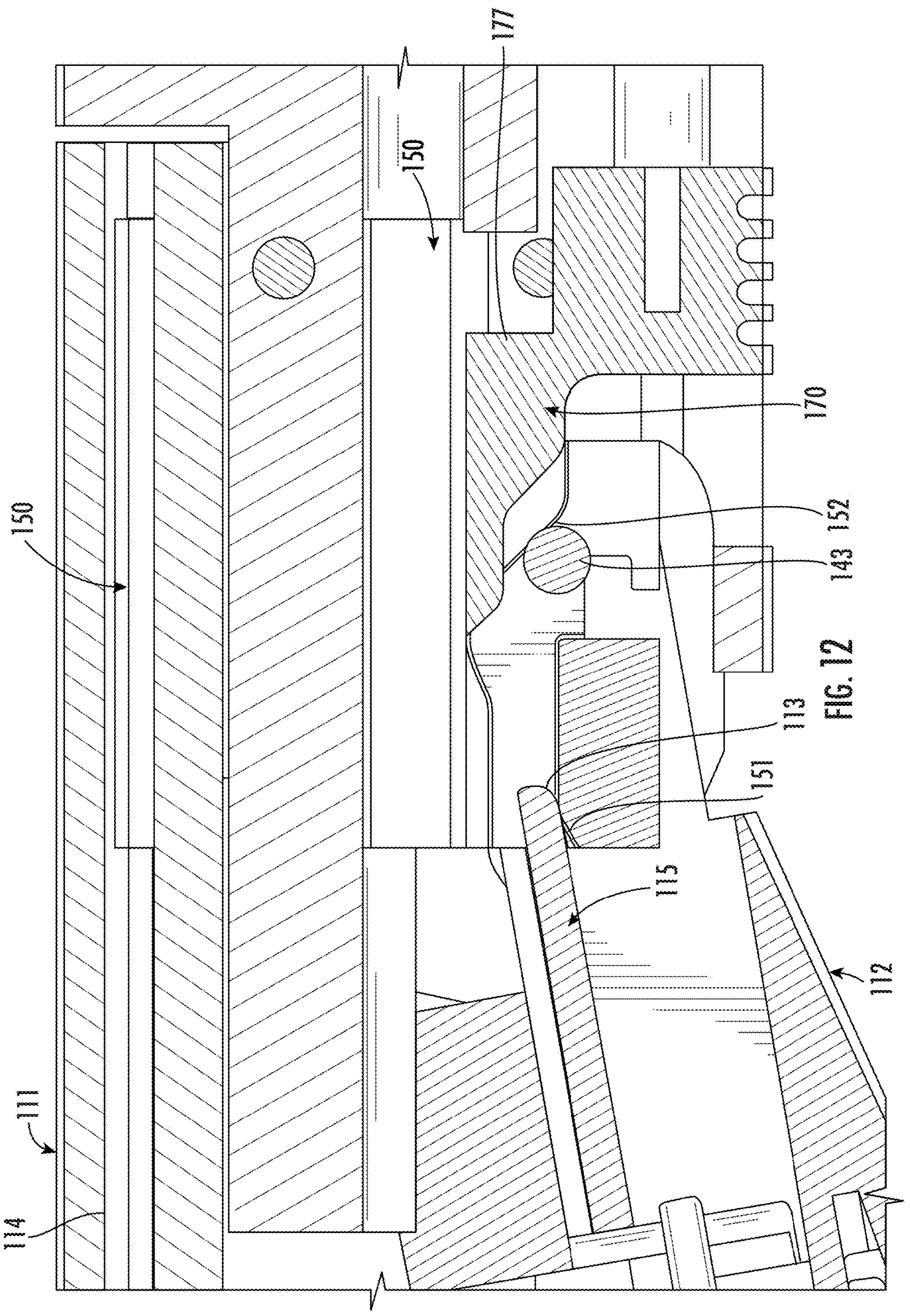
FIG. 12 is a partial perspective view of the end effector of the surgical instrument of FIG. 1 depicting a drive member translating distally to begin closing the jaws.

FIGS. 12 and 13 depict the closing of the jaws of surgical instrument 100 to clamp tissue.

In FIG. 12, upon an input command being given to a robotic surgical system to grasp tissue, or upon manual activation of a trigger or handle as are known by those of skill in the art, drive member 150 travels distally, causing a lower distal ramped surface 151 of drive member 150 to engage ramped surface 113 on channel 115 of removable jaw 112, forcing removable jaw 112 to move towards anvil 114, thereby urging the jaws towards a closed position. Simultaneously, proximal ramped surface 152 of drive member 150 pushes proximal pin 143 downwards as drive member 150 translates distally.

Figure 13A:
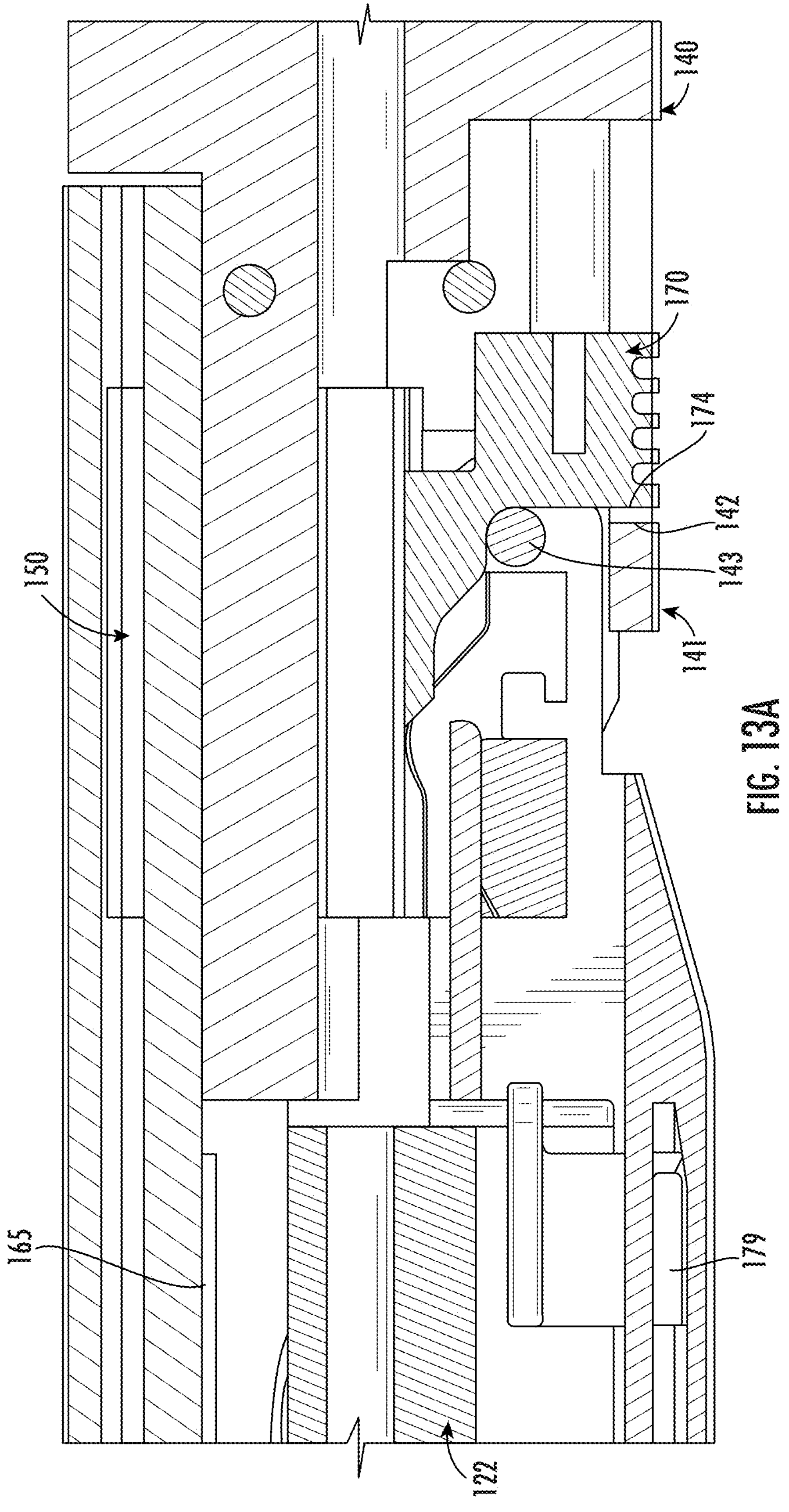
FIG. 13A is a partial perspective view of the end effector of the surgical instrument of FIG. 1 in the closed and clamped position.
Figure 13B:
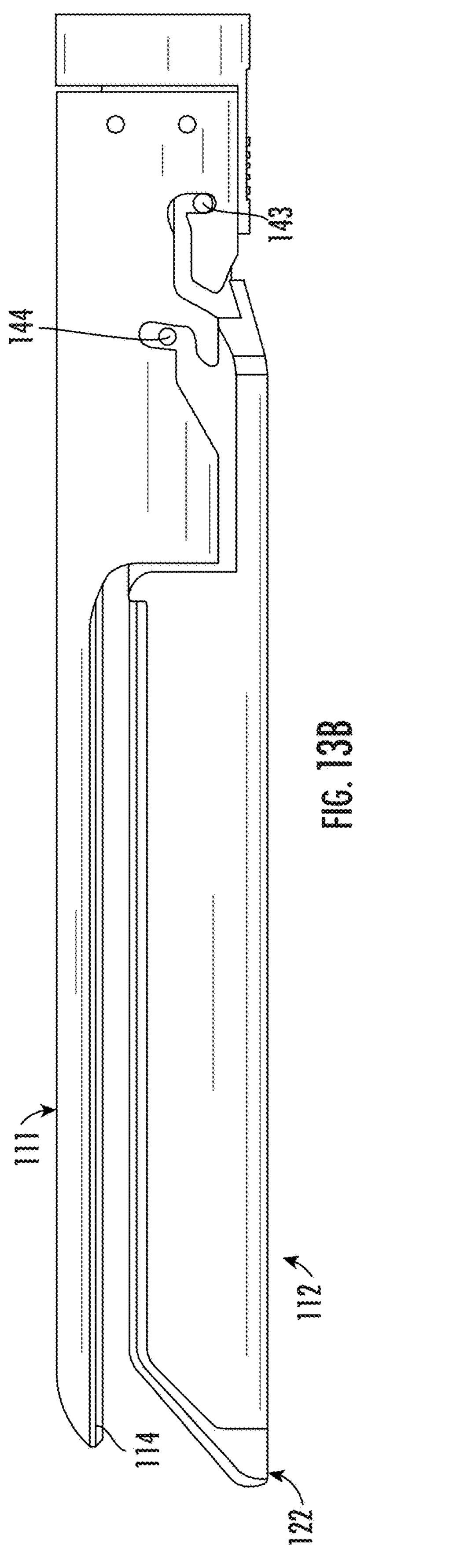
FIG. 13B is a partial perspective view of the end effector of the surgical instrument of FIG. 5 shown in a second closed position providing for a tissue gap.
Figure 13C:
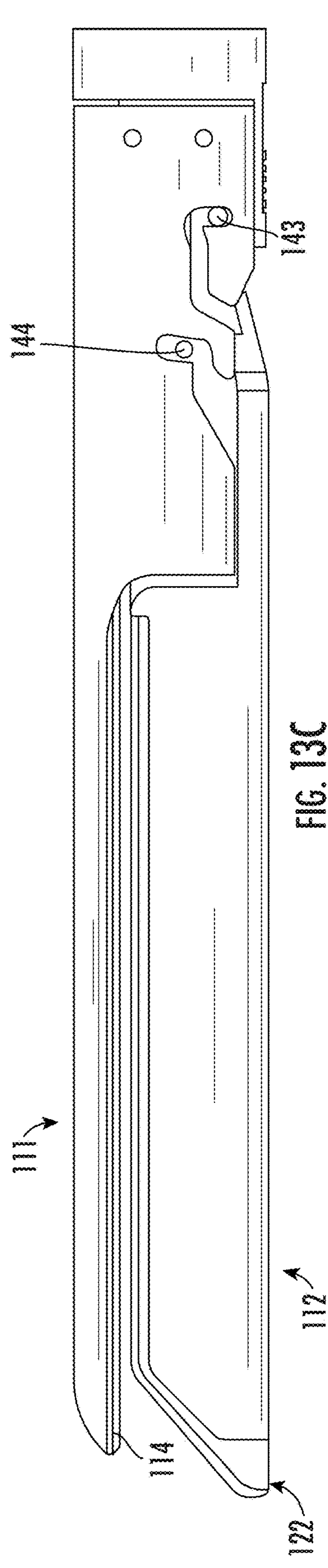
FIG. 13C is a partial perspective view of the end effector of the surgical instrument of FIG. 6 shown in a second closed position providing for a tissue gap.
Figure 14:
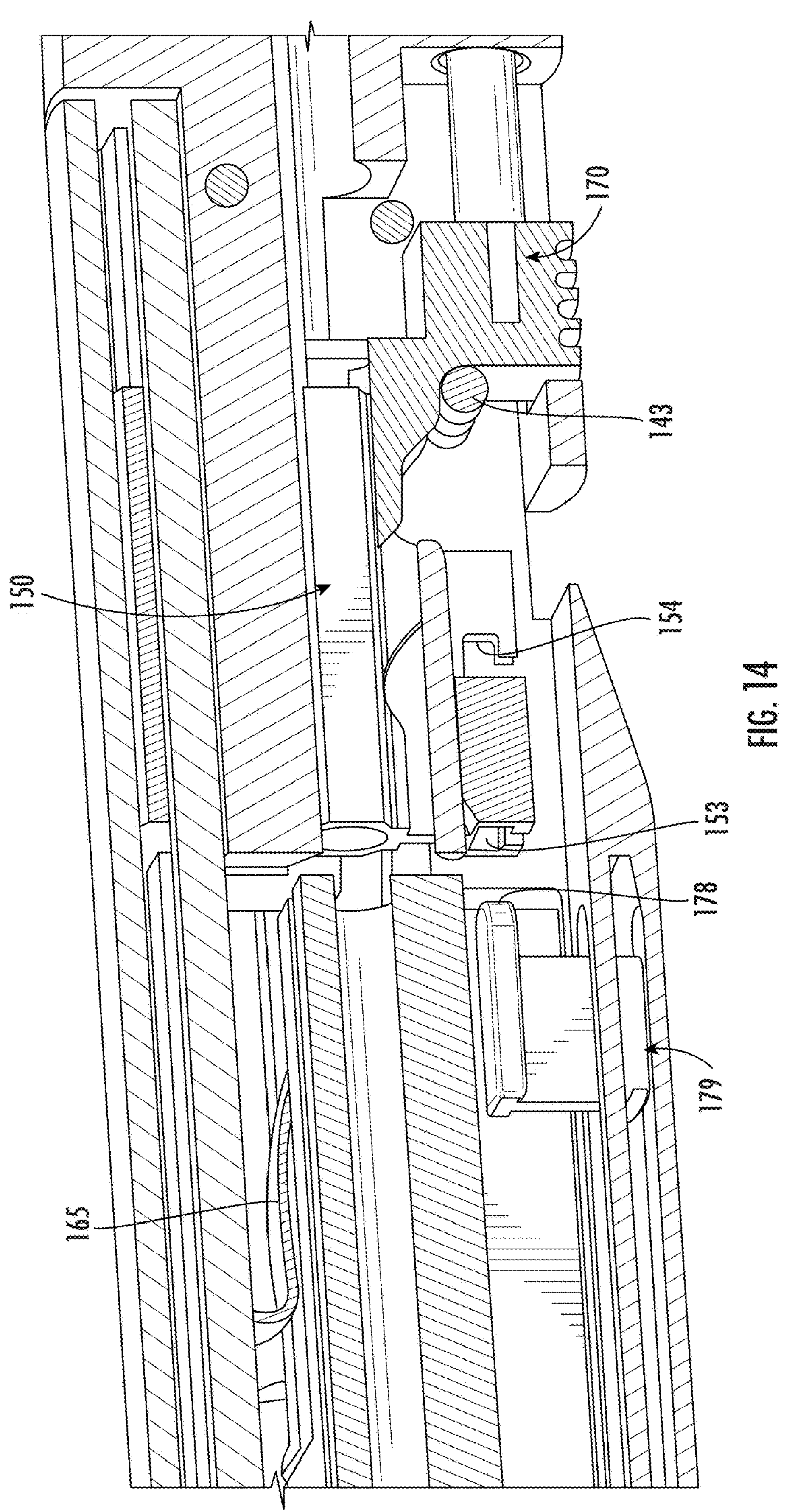
FIG. 14 is a partial perspective view of the end effector of the surgical instrument of FIG. 1 having a drive member that is translating distally to pick up a secondary drive member during actuation of the surgical instrument.

In FIG. 13A, the jaws of surgical instrument 100 are fully closed, tissue is clamped, and instrument 100 is prepared for actuation to staple and sever clamped tissue. In this position, drive member 150 has continued to travel distally and has caused the jaws 111,112 to pivot to the second closed position providing for a tissue gap between jaws 111, 112. The second closed positions are best illustrated and described below in connection with FIGS. 13B and 13C. In FIG. 13A, drive member 150 has also pushed proximal pin 143 further downwards within proximal slot 180, causing removable jaw 112 to translate downwards in relation to stationary jaw 111. In this position, secondary drive member 179 has been consequently translated downwards into proper alignment with drive member 150 as shown in FIG. 14 below. Once pin 143 has cleared proximal ramped surface 152 of drive member 150, the bias of latch spring 175 forces latch 170 to translate distally, causing a distal locking edge 177 of latch 170 to trap proximal pin 143 in a predetermined, second locked position in which it is substantially unable to move. Distal locking edge 177 of latch 170 is unable to trap proximal pin 143 in the second locked position before drive member 150 has translated far enough distally to drive proximal pin 143 towards the bottom of proximal slot 180, because an edge 156 of drive member 150 interferes with and abuts distal locking edge 177 of latch 170. Once drive member 150 begins to translate distally, spring 175 will force latch 170 to also translate distally until a lower distal surface 174 of latch 170 engages and abuts a proximal surface 142 of clevis protrusion 141 such that latch 170 remains in the proper position to trap proximal pin 143. In this configuration, the tissue gap of surgical instrument 100, as determined by the height of secondary drive member 179 is provided for. One of ordinary skill will appreciate that proximal pin 143 will ultimately be trapped in the second locked position in which it is substantially unable to move regardless of the height of secondary drive member 179 and the size of the tissue gap provided for in a given removable jaw 112 secured within stationary jaw 111 of surgical instrument 100.

FIG. 13B depicts the end effector and removable jaw of the embodiment shown in FIG. 5 in the second closed position providing for a first tissue gap. FIG. 13C depicts the end effector and removable jaw shown in FIG. 6 in a second closed position providing for a second tissue gap that is thinner than the first tissue gap shown in FIG. 13B. As described above, proximal pin 143 remains stationary in in the predetermined second locked position in both embodiments despite removable jaw 112 being of a different size and configured to provide for a unique tissue gap in each embodiment. Surgical instrument 100 is now prepared for actuation to grasp, sever, and staple grasped tissue.

In an alternative embodiment, surgical instrument 100 is configured to adjust the position of the removable jaw or reload 112 in the second or extended closed position such that an individual reload may be moved into different extended closed positions relative to jaw 111, thereby creating different tissue gaps with the same reload 112. In this embodiment, it may not be necessary to install a second reload onto surgical instrument 100 in order to change the size of the tissue gap between jaws 111, 112. In certain embodiments, latch 170 may include one or more camming surfaces (not shown) configured to move pin 143 of jaw 112 into multiple vertical positions within proximal slot 180. For example, latch 170 may be configured to translate distally a first distance, thereby camming pin 143 vertically downwards a first distance that provides a first tissue gap between jaws 111, 112. Latch 170 may then be configured to translate distally a second distance greater than the first distance, thereby camming pin 143 vertically downwards a second distance to provide a larger tissue gap between jaws 111, 112.

Figure 15:
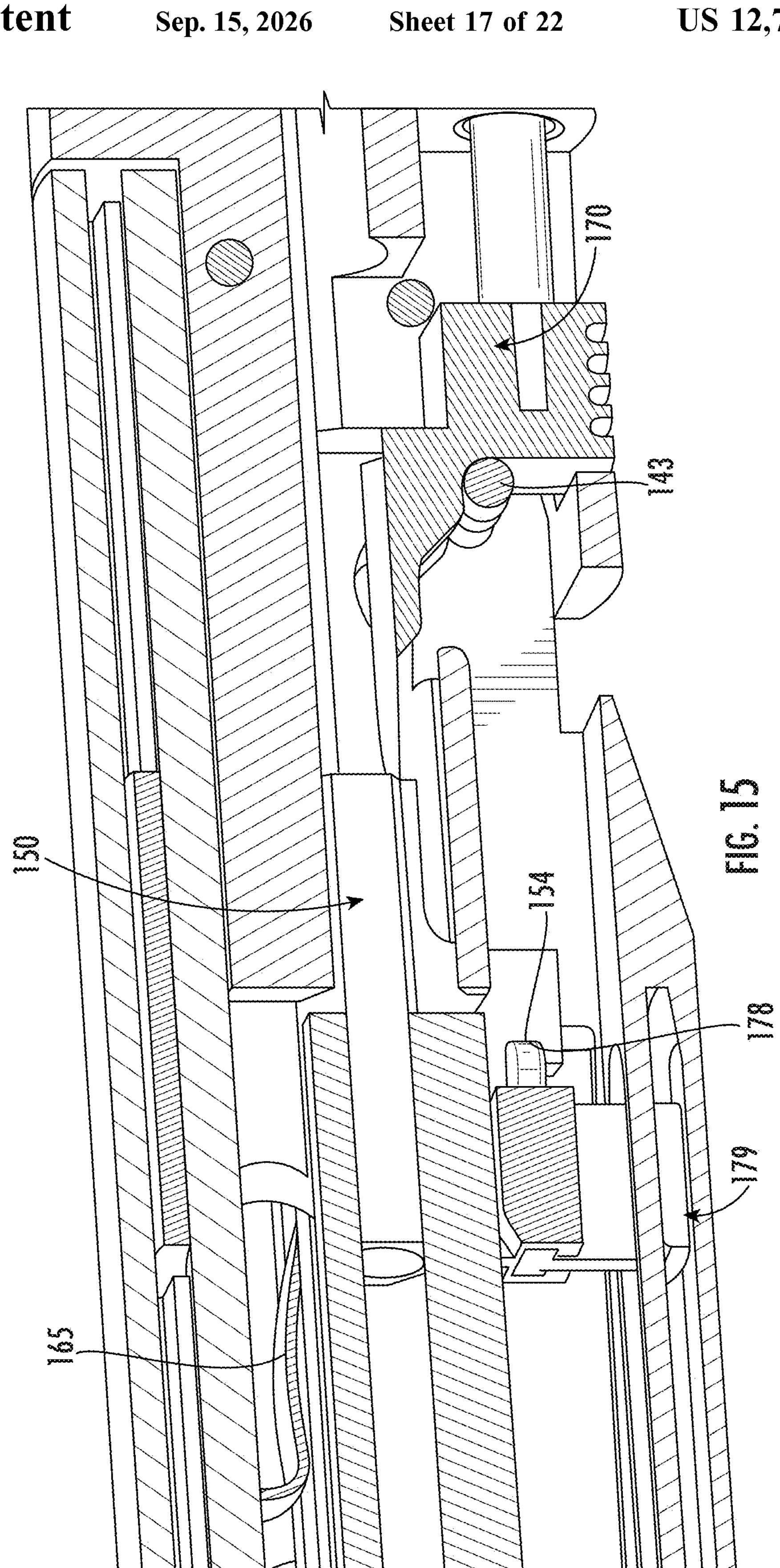
FIG. 15 is a partial perspective view of the end effector of the surgical instrument of FIG. 1 depicting a drive member and a secondary drive member moving distally together through the end effector to sever and staple tissue.
Figure 16:
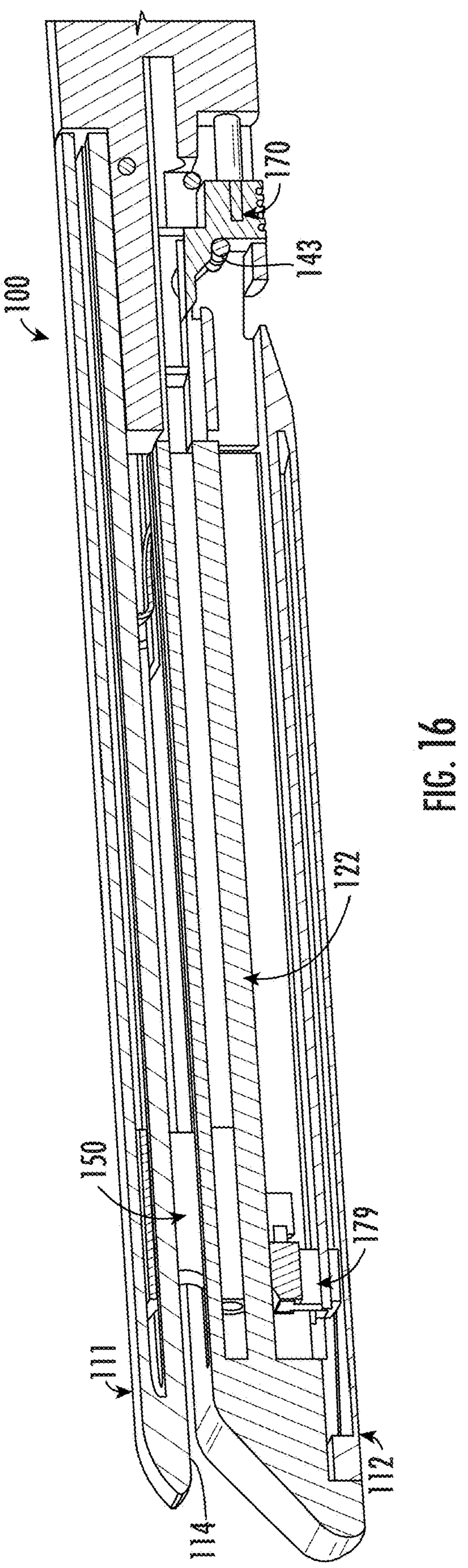
FIG. 16 is a partial perspective view of the end effector of the surgical instrument of FIG. 1 after the surgical instrument has been actuated with the drive members at the distal end of the end effector.

FIGS. 14-16 depict actuation of surgical instrument 100 to staple and sever clamped tissue.

FIG. 14 shows drive member 150 being driven distally upon actuation of surgical instrument 100. Known actuation mechanisms and backend mechanisms, such as those previously referenced above, cause drive member 150 to travel distally through the end effector. As shown in FIG. 15, as drive member 150 continues to translate distally, it picks up secondary drive member 179 as proximal tab 178 of secondary drive member 179 passes into a slot 153 of drive member 150. As drive member 150 continues translating distally, lower distal surface 154 of drive member 150 will engage proximal tab 178 on secondary drive member 179. In embodiments, drive member 150 may be an upper portion of an I-beam, and secondary drive member 179 may be an I-beam footer that is "picked up" upon distal translation of drive member 150 forming an I-Beam.

In FIG. 16, drive member 150 and secondary drive member 179 have translated to the distal end of surgical instrument 100, stapling and severing tissue through interaction with the components of cartridge 122 as described above. Upon completion of a firing stroke, the surgical instrument 100 may be removed from the surgical site and the drive member 150 may be retracted by the actuation mechanism (not expressly shown) so that surgical instrument 100 returns to the passively open position shown in FIG. 11. However, removable jaw 112 remains secured to surgical instrument 100 until released by a user.

Figure 17A:
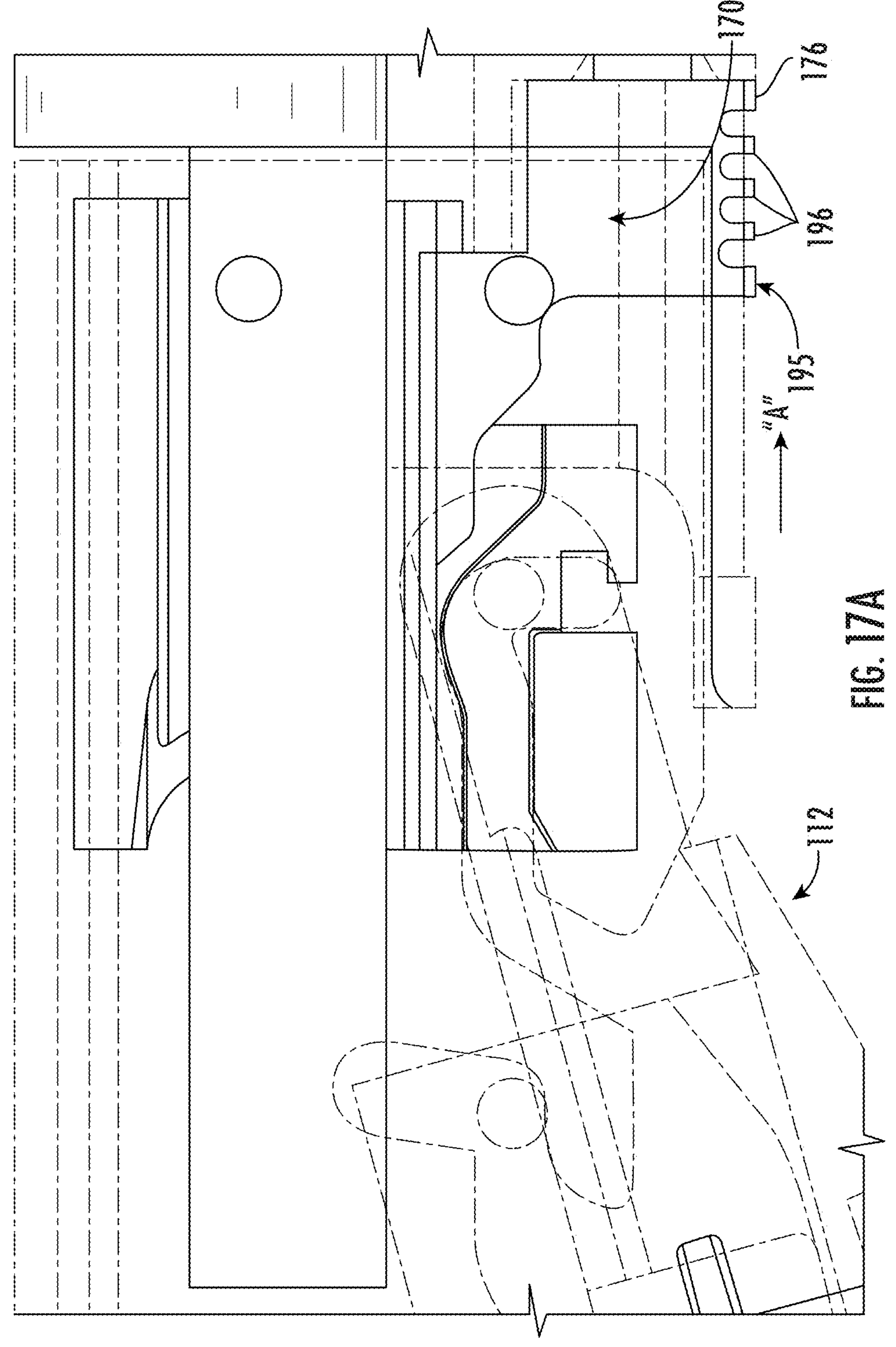
FIG. 17A is a partial perspective view of the end effector of the surgical instrument of FIG. 1 depicting a mechanism for releasing the reload.
Figure 17B:
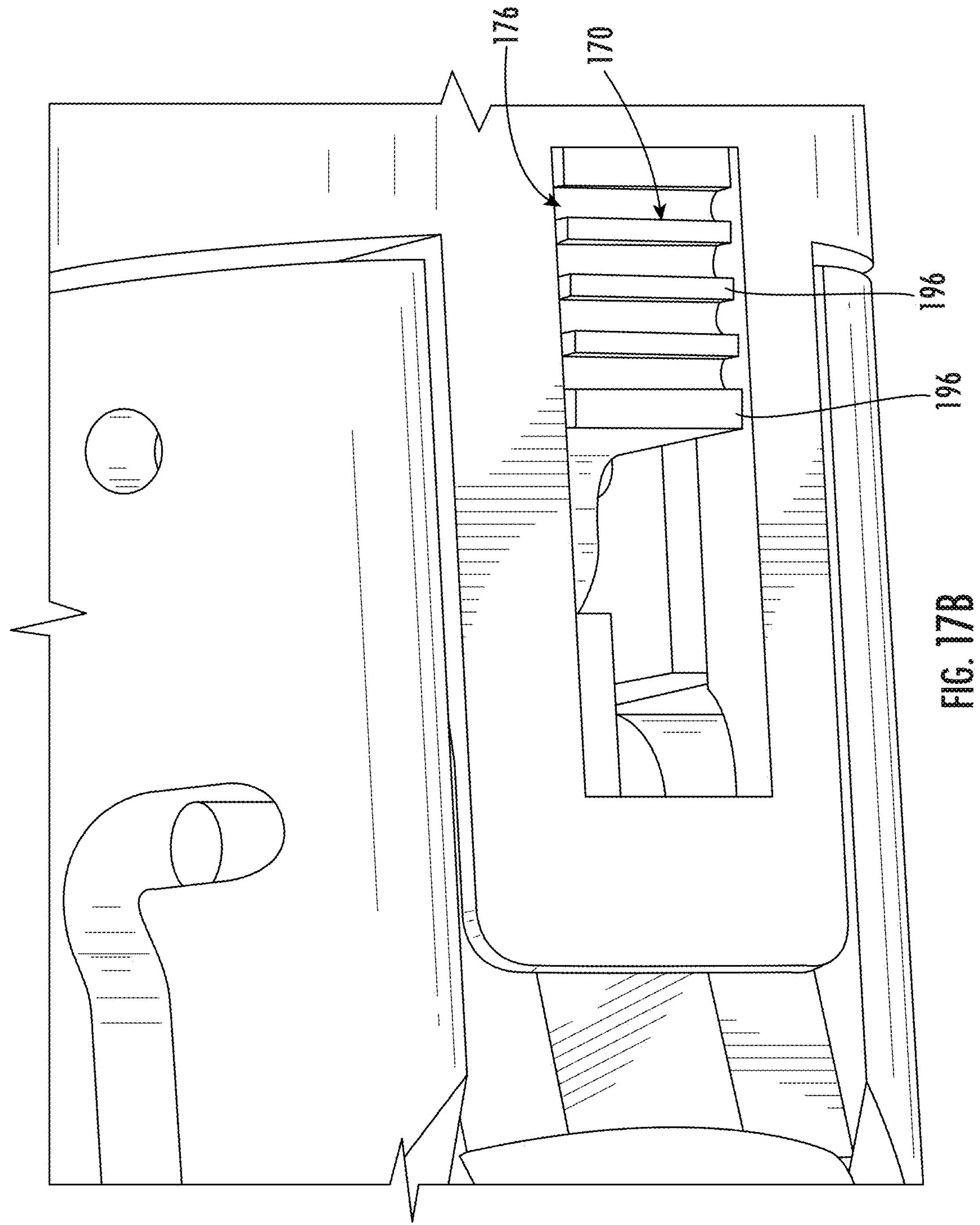
FIG. 17B is a partial bottom view of the end effector of the surgical instrument of FIG. 1 depicting the mechanism for releasing the reload.

FIGS. 17A and 17B illustrate a mechanism for releasing removable jaw 112 from surgical instrument 100.

In FIG. 17A, latch 170 includes a latch release 195 on bottom face 176 of latch member 170. Bottom face 176 of latch release 195 protrudes out of a window 199 on the bottom of movable jaw 112 such that a user may manually activate latch release 195 to release a reloadable portion 112 after firing. As shown in FIG. 17B, bottom face 176 of latch 170 may have grooves 196 to facilitate manual activation of latch release 195, however, bottom face 176 of latch 170 may include other features to facilitate use such as a protrusion, a recess, or any other design to facilitate manually activating latch release 195. When bottom face 176 is manually pulled in the proximal direction shown by Arrow "A" overcoming the bias of latch spring 175, latch 170 translates proximally, freeing proximal pin 143 and allowing for removal of removable jaw 112.

Figure 18:
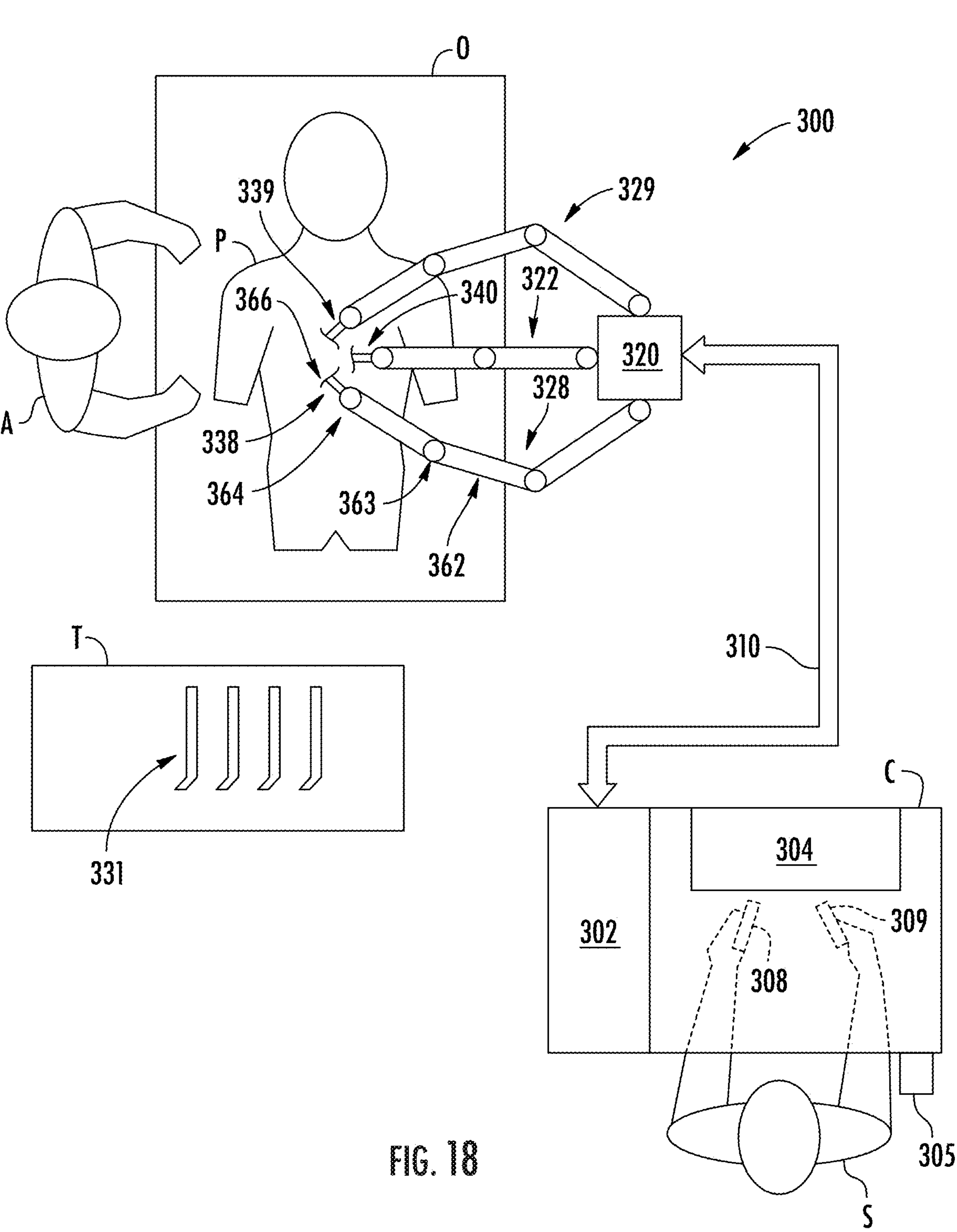
FIG. 18 illustrates a top view of an operating room employing a robotic surgical system utilizing aspects of the present disclosure.

The present surgical instrument may be used in a robotic surgical system. FIG. 18 illustrates, as an example, a top view of an operating room employing a robotic surgical system. The robotic surgical system in this case is a robotic surgical system 300 including a console ("C") utilized by a surgeon ("S") while performing a minimally invasive diagnostic or surgical procedure, usually with assistance from one or more assistants ("A"), on a patient ("P") who is lying down on an operating table ("O").

The console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware.

For additional details on robotic surgical systems, see, e.g., U.S. Pat. Nos. 6,493,608 and 6,671,581, the entire contents of which are incorporated herein by this reference.

Figure 19:
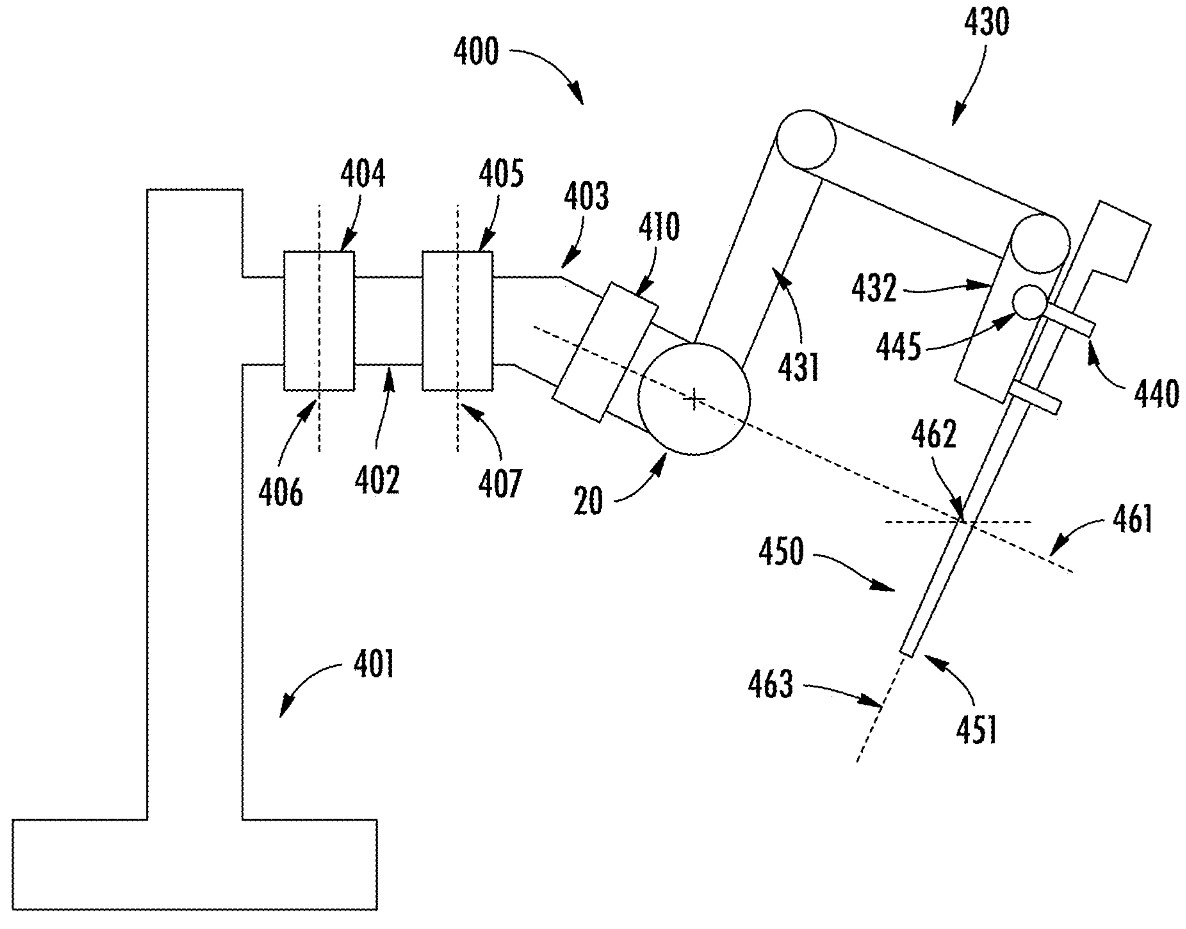
FIG. 19 illustrates a simplified side view of a robotic arm assembly that is usable with various aspects of the present disclosure.

FIG. 19 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403 which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407.

Although only two links and two setup joints are shown in this example, more or less of each may be used as appropriate in this and other robotic arm assemblies in conjunction with the present disclosure. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator.

While several embodiments have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

What is claimed:

1. A surgical instrument comprising:

an elongate shaft having an end effector;

a first drive member configured to translate distally through a portion of the end effector, the first drive member including a first flange at a first end thereof and a first engagement structure at an opposite end thereof; and a first staple cartridge couplable to the end effector and having a secondary drive member including a second flange at a first vertical distance from a second engagement structure, the second engagement structure being configured to engage the first engagement structure such that, when the first staple cartridge is coupled to the end effector, a first tissue gap distance may be established by the first flange of the first drive member and the second flange of the first staple cartridge; and a second staple cartridge couplable to the end effector and having another secondary drive member including a third flange at a second vertical distance, different from the first vertical distance, from a third engagement structure, the third engagement structure being configured to engage the first engagement structure such that, when the second staple cartridge is coupled to the end effector, a second tissue gap distance, different from the first tissue gap distance, may be established by the first flange of the first drive member and the third flange of the second staple cartridge.

2. The surgical instrument of claim 1, wherein the first engagement structure is a slot and the second and third engagement structures are tabs configured to be received within the slot.

3. The surgical instrument of claim 1, wherein the end effector comprises a first jaw and the first and second staple cartridges each comprise a second jaw, wherein the first flange is configured to translate through a channel in the first jaw of the end effector, and the second and third flanges are configured to translate through a channel in the respective second jaw.

4. The surgical instrument of claim 3, wherein at least one of the first jaw and second jaws of the respective first and second staple cartridges are movable between an open position and a closed position to grasp tissue between the first jaw and second jaw via translation of the first flange through the channel in the first jaw and translation of the second or third flanges through the channels in the respective second jaws.

5. The surgical instrument of claim 4, further comprising the first staple cartridge coupled to the end effector, the first jaw and the second jaw of the first staple cartridge in the closed position such that the first tissue gap is established as a result of the translation of the first flange through the first channel of the first jaw and the second flange through the second channel of the second jaw of the first staple cartridge.

6. The surgical instrument of claim 4, further comprising the second staple cartridge coupled to the end effector, the first jaw and the second jaw of the second staple cartridge in the closed position such that the second tissue gap is established as a result of the translation of the first flange through the first channel of the first jaw and the third flange through the second channel of the second jaw of the second staple cartridge.

7. The surgical instrument of claim 1, wherein the first drive member and a selected one of the secondary drive members collectively form an I-beam upon engagement of the first engagement structure with the second or third engagement structure.

8. The surgical instrument of claim 1, further comprising a spring on a stationary jaw of the end effector, the spring configured to bias the selected first or second staple cartridge towards an open position.

9. The surgical instrument of claim 1, wherein the first drive member further includes a distal ramped surface configured to engage a surface of the first or second staple cartridge to pivot the staple cartridge toward a closed position upon distal translation of the first drive member.

* * * * *